(12) United States Patent
Stayshich et al.

(10) Patent No.: US 11,897,894 B2
(45) Date of Patent: Feb. 13, 2024

(54) INDOLENAPHTHOPYRANS

(71) Applicant: Transitions Optical, Ltd., Tuam (IE)

(72) Inventors: Ryan Stayshich, Pittsburgh, PA (US); Zachary Smith, Pittsburgh, PA (US); Robert W. Walters, Murrysville, PA (US)

(73) Assignee: Transitions Optical, Ltd., Tuam (IE)

( * ) Notice: Subject to any disclaimer, the term of this patent is extended or adjusted under 35 U.S.C. 154(b) by 351 days.

(21) Appl. No.: 17/416,006

(22) PCT Filed: Dec. 21, 2018

(86) PCT No.: PCT/EP2018/086583
§ 371 (c)(1),
(2) Date: Jun. 18, 2021

(87) PCT Pub. No.: WO2020/126030
PCT Pub. Date: Jun. 25, 2020

(65) Prior Publication Data
US 2021/0317129 A1 Oct. 14, 2021

(51) Int. Cl.
*C09K 9/02* (2006.01)
*C07D 491/052* (2006.01)
*G02B 1/04* (2006.01)

(52) U.S. Cl.
CPC ............ *C07D 491/052* (2013.01); *C09K 9/02* (2013.01); *G02B 1/043* (2013.01); *C09K 2211/1033* (2013.01)

(58) Field of Classification Search
CPC .................. C07D 491/052; C09K 9/02; C09K 2211/1033; G02B 1/043
See application file for complete search history.

(56) References Cited

U.S. PATENT DOCUMENTS

| | | | |
|---|---|---|---|
| 5,645,767 A | 7/1997 | Van Gemert | |
| 6,113,814 A | 9/2000 | Gemert et al. | |
| 6,296,785 B1 * | 10/2001 | Nelson | G02B 5/23 |
| | | | 544/150 |
| 6,392,043 B1 * | 5/2002 | Bourchteine | C07D 311/78 |
| | | | 548/418 |
| 6,555,028 B2 | 4/2003 | Walters et al. | |
| 7,262,295 B2 | 8/2007 | Walters et al. | |
| 8,308,996 B2 | 11/2012 | Takahashi et al. | |
| 8,608,988 B2 | 12/2013 | Bowles et al. | |
| 9,028,728 B2 | 5/2015 | Bancroft et al. | |
| 2011/0216273 A1 * | 9/2011 | He | C09K 19/54 |
| | | | 349/158 |

FOREIGN PATENT DOCUMENTS

| | | |
|---|---|---|
| EP | 2463280 A1 | 6/2012 |
| JP | 2000229974 A | 8/2000 |
| JP | 2003277381 A | 10/2003 |
| WO | 9923071 A1 | 5/1999 |
| WO | 2016142496 A1 | 9/2016 |
| WO | 2017030545 A1 | 2/2017 |

* cited by examiner

OTHER PUBLICATIONS

Hansch et al., "A Survey of Hammett Substituent Constants and Resonance and Field Parameters," 1991, Chem Rev., pp. 165-195, vol. 91.

*Primary Examiner* — Bijan Ahvazi
(74) *Attorney, Agent, or Firm* — The Webb Law Firm

(57) ABSTRACT

Provided is a photochromic indolenapthtopyran having the core skeletal structure of Formula (I): wherein $R^1$ and $R^2$ are each independently substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, a nitrogen-containing heterocycle, substituted or unsubstituted alkyl, substituted or unsubstituted (Continued)

aryl, —NHC(O)R$^a$, or —OC(O)R$^a$, wherein R$^a$ is substituted or unsubstituted alkyl, substituted or unsubstituted aryl, substituted or unsubstituted heteroaryl, substituted or unsubstituted alkoxy, substituted or unsubstituted aryloxy, substituted or unsubstituted alkylthio, or substituted or unsubstituted arylthio; R$^4$ is selected from hydrogen, substituted or unsubstituted alkyl, substituted or unsubstituted heterocycloalkyl, allyl, substituted or unsubstituted aryl, or substituted or unsubstituted heteroaryl; and B and B' are each independently substituted or unsubstituted aryl, or substituted or unsubstituted heteroaryl, wherein each substituted aryl or substituted heteroaryl is substituted with a group having a Hammett $\sigma_p$ value of greater than −0.50.

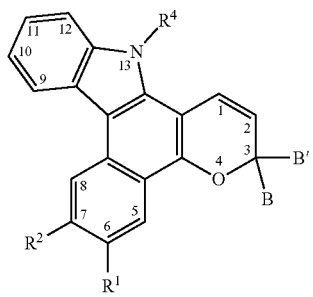

(I)

15 Claims, 1 Drawing Sheet

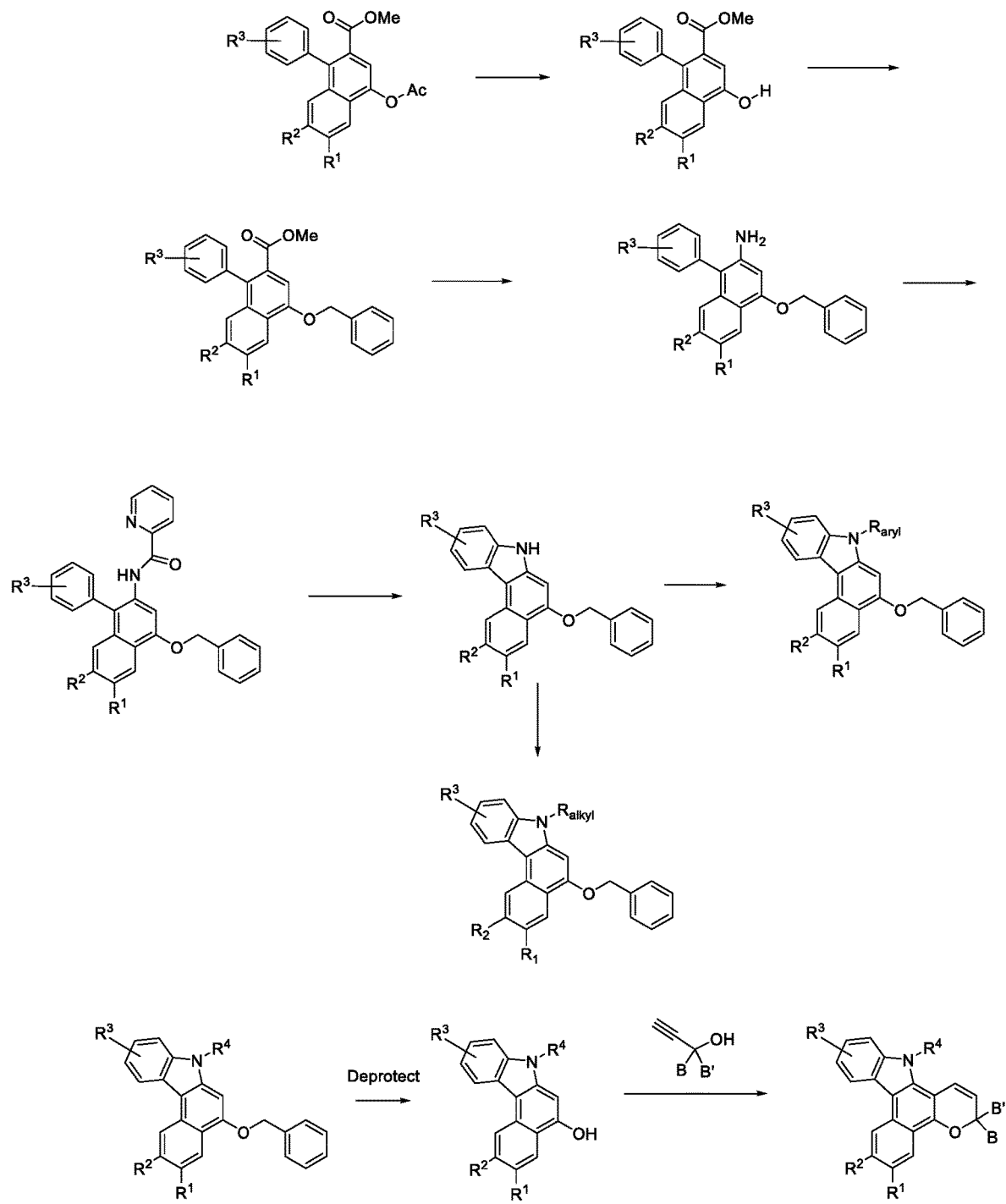

INDOLENAPHTHOPYRANS

FIELD

The present invention relates to photochromic compounds, such as photochromic indolenaphthopyran compounds, and photochromic compositions and photochromic articles that include such photochromic compounds.

BACKGROUND

Photochromic compounds undergo a transformation from one state (or form) to another state in response to certain wavelengths of electromagnetic radiation (e.g., "actinic radiation"). Each state has a characteristic absorption spectrum. For example, many photochromic compounds transform from an unactivated (e.g., bleached or substantially colorless) state to an activated (e.g., tinted) state upon exposure to actinic radiation. When the actinic radiation is removed, the photochromic compounds reversibly transform from the activated state back to the unactivated state.

Photochromic compounds can be characterized with regard to various properties, such as but not limited to: fade rate; change in optical density (ΔOD); the change in optical density (ΔOD) at saturation; sensitivity (ΔOD/Min); the efficiency at which the photochromic compound absorbs radiation required to activate the photochromic compound (chromaticity); and dichroic properties such as in the case of photochromic-dichroic compounds, which can be quantified with regard to absorption ratio (AR) values. The change in optical density measures the change from the unactivated state to the activated state.

Some photochromic compounds have a bimodal absorption profile, having an absorption band "A" (hereinafter referred to as "A band") which is of greater intensity than the absorption band "B" (hereinafter referred to as "B band"). The absorption of the A band occurs in the 420-500 nm region while the absorption of B band occurs in the 500-650 nm region of the activated visible spectrum.

It is desirable for photochromic ophthalmic lenses to have a grey, green, or brown hue in the activated state. These colors can be obtained by mixing photochromic compounds that have different activated colors in ratios to generate the grey, brown, or green color spaces. The yellow colored naphthopyrans have inherent weakness in durability and often degrade at rates much faster than purple or blue photochromic compounds of the indeno-fused naphthopyran families. Broad band absorbing indeno-fused compounds have been used to overcome the limitations of yellow naphthopyrans, but indeno-fused naphthopyrans that are yellow (high b*) in activated color are still difficult to obtain.

Indenonaphthopyran compounds are known in the art as having an A band to B band absorption ratio of 1-2:1 to yield olive colored dyes. Indeno-fused compounds exemplified in U.S. Pat. No. 6,296,785, such as the compound below, were shown to have an improved A band to B band absorption ratio of 1.65 relative to other indeno-fused compounds.

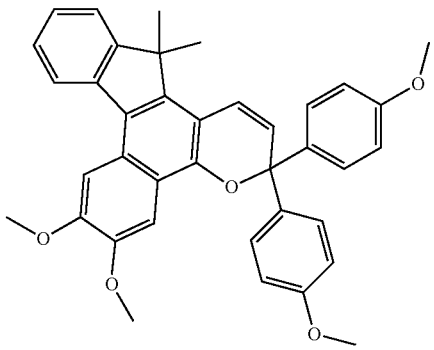

Indeno-fused compounds from U.S. Pat. No. 8,308,996, such as the compound below, were shown to have an improved A band to B band absorption ratio of 1.50 relative to other indeno-fused compounds.

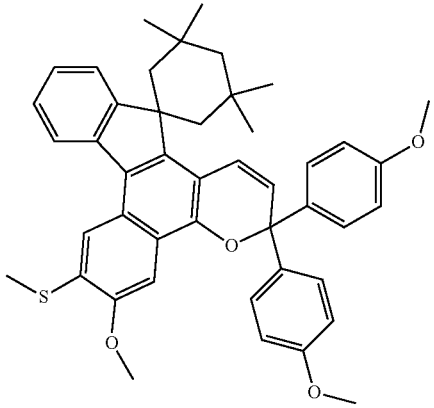

The indolenephthopyrans described herein can unexpectedly provide an A band to B band absorption ratio of at least 3 to 7:1. These ratios yield green, brown, and pure yellow colored dyes. Pure yellow colored dyes with very little photopic absorption are ideal for blue light filtering devices. It is desirable to have a durable photochromic compound that can absorb preferentially in the high energy region of the visible spectrum (i.e., in the 380-500 nm region) to block harmful blue light. The deleterious effects of blue light, such as cataracts, macular degeneration, and disruption of circadian rhythms, are well documented and many fixed tint products have been produced to help block this harmful blue light. A product that can become more blue light blocking when exposed to sunlight is desired as high levels of blue light is present in sunlight.

The indolenaphthopyrans of the present invention provide enhanced A band to B band absorption ratios by balancing the effects of the substituents described herein. Indolenaphthopyrans compounds with specific substitutions at the 6 and 7 position combined with certain groups on the B and B' positions of Formulas (I) and/or (Ia) described herein have much higher activated yellowness (b*) and A band to B band absorption ratios than known indolenaphthopyrans. These novel compounds have A band to B band absorption ratios of greater than 3:1 and in some cases greater than 6:1, such as 3 to 7:1, such as 3 to 6.5:1, such as 3 to 6.4:1, or such as 3.45 to 6.4:1.

These compounds also are much more resistant to photodegradation than yellow naphthopyrans and match the durability of purple/blue indeno-fused naphthopyrans. These novel compounds can be used to produce new improved products over other known compounds that can protect users from the harmful effects of solar energy.

It would be desirable to provide a photochromic compound having enhanced A band to B band absorption ratios for improved color, and blue light and UV attenuation. For example, it would be desirable to provide new photochromic indolenaphthopyran compounds with such features.

SUMMARY

A photochromic compound comprises a core skeletal structure represented by the following Formula (I),

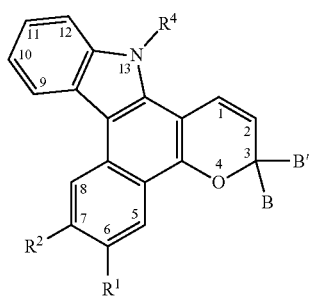

Formula (I)

wherein, $R^1$ and $R^2$ are each independently substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, a nitrogen containing heterocycle, substituted or unsubstituted alkyl, substituted or unsubstituted aryl, —NHC(O)$R^a$, or —OC(O)$R^a$, wherein $R^a$ is substituted or unsubstituted alkyl, substituted or unsubstituted aryl, substituted or unsubstituted heteroaryl, substituted or unsubstituted alkoxy, substituted or unsubstituted aryloxy, substituted or unsubstituted alkylthio, or substituted or unsubstituted arylthio; $R^4$ is selected from hydrogen, substituted or unsubstituted alkyl, substituted or unsubstituted heterocycloalkyl, allyl, substituted or unsubstituted aryl, or substituted or unsubstituted heteroaryl; and B and B' are each independently substituted or unsubstituted aryl, or substituted or unsubstituted heteroaryl, wherein each substituted aryl or substituted heteroaryl is substituted with a group having a Hammett $\sigma_p$ value of greater than −0.50.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWING

FIG. 1 illustrates a general scheme, Scheme 1, of an exemplary method for preparing photochromic compounds of the invention.

DETAILED DESCRIPTION

As used herein, the articles "a", "an", and "the" include plural referents unless otherwise expressly and unequivocally limited to one referent.

As used herein, the term "includes" is synonymous with "comprises".

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

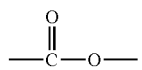

or equivalently —C(O)O—, is inclusive of the right-to-left representation thereof,

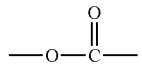

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about." By "about" is meant plus or minus twenty-five percent of the stated value, such as plus or minus ten percent of the stated value. However, this should not be considered as limiting to any analysis of the values under the doctrine of equivalents.

As used herein, molecular weight values of polymers, such as weight average molecular weights (Mw) and number average molecular weights (Mn), are determined by gel permeation chromatography using appropriate standards, such as polystyrene standards.

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means derivatives of acrylic acid and methacrylic acid, inclusive of acrylate esters, methacrylate esters, acrylamides, methacrylamides, acrylic acid and methacrylic acid. As used herein, the term "(meth)acrylic acid" means methacrylic acid and/or acrylic acid.

The photochromic compounds of the present invention are, with some embodiments, also referred to herein as photochromic-dichroic compounds (such as, when they include one or more mesogen-containing groups, such as $L^1$).

The photochromic compounds of the present invention, as described herein, including, but not limited to, photochromic compounds represented by Formula (I) and Formula (Ia), in each case can optionally further include one or more coproducts, resulting from the synthesis of such compounds.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "dichroic" means capable of absorbing one of two orthogonal plane polarized components of at least transmitted radiation more strongly than the other.

As used herein, the term "photochromic-dichroic" and similar terms, such as "photochromic-dichroic compound", means possessing and/or providing both photochromic properties (i.e., having an absorption spectrum for at least visible radiation that varies in response to at least actinic radiation), and dichroic properties (i.e., capable of absorbing one of two orthogonal plane polarized components of at least transmitted radiation more strongly than the other).

As used herein, and unless stated otherwise or otherwise limited, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein, to modify the term "state", the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein, the term "optical" means pertaining to or associated with light and/or vision. For example, according to various non-limiting embodiments disclosed herein, the optical article or element or device can be chosen from ophthalmic articles, elements and devices; display articles, elements and devices; windows; mirrors; or active and passive liquid crystal cell articles, elements and devices.

As used herein, the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein, the term "display" means the visible or machine-readable representation of information in words, numbers, symbols, designs or drawings. Non-limiting examples of display elements include screens, monitors, and security elements, such as security marks.

As used herein, the term "window" means an aperture adapted to permit the transmission of radiation therethrough. Non-limiting examples of windows include automotive and aircraft transparencies, windshields, filters, shutters, and optical switches.

As used herein, the term "mirror" means a surface that specularly reflects a large fraction of incident light.

As used herein, the term "liquid crystal cell" refers to a structure containing a liquid crystal material that is capable of being ordered. A non-limiting example of a liquid crystal cell element is a liquid crystal display.

As used herein, the terms "formed over", "deposited over", "provided over", "applied over", "residing over", or "positioned over" mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, recitations relating to ring positions such as, but not limited to, position-x (e.g., position-3 or position-13) means a particular position in the ring structure, such as the core skeletal structure, of a chemical compound, such as the indolenaphthopyran photochromic compounds of the present invention, and which are depicted herein in accordance with some embodiments by numbers within the ring structures of representative chemical formulas such as, but not limited to Formulas (I) and/or (Ia).

By "core skeletal structure" is meant a compound comprising at least the skeletal structure depicted in the associated Formula. The core skeletal structure is provided for purposes of identifying numbered ring positions. However, it is to be understood that, unless specifically shown to the contrary, the core skeletal structure(s) can have one or more atoms or one or more groups (not specifically illustrated on the corresponding Formula) bonded to one or more of the numbered ring positions on the core skeletal structure, which can be the same or different from one another.

The photochromic compounds of the present invention are referred to herein with reference to the term "core skeletal structure", which can be represented by one or more formulas, such as but not limited to Formulas (I) and/or (Ia).

All documents or portions of documents, such as but not limited to issued patents and patent applications, referred to herein, and unless otherwise indicated, are to be considered to be "incorporated by reference" in their entirety.

"Aryl group" refers to an aromatic cyclic monovalent hydrocarbon radical, and the term "aromatic" refers to a cyclically conjugated hydrocarbon with a stability (due to delocalization) that is significantly greater than that of a hypothetical localized structure. Examples of aryl groups include $C_6$-$C_{14}$ aryl groups, such as, but not limited to, phenyl, naphthyl, phenanthryl, and anthracenyl.

As used herein, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to, perhaloalkyl groups, perhaloalkenyl groups, perhaloalkynyl groups, perhaloaryl groups or perhalo-heteroaryl groups) means a group in which all of the available hydrogen groups thereof are substituted with a halo group. For example, perhalomethyl is —$CX_3$; perhalophenyl is —$C_6X_5$, where X represents one or more halo groups, such as, but not limited to F, Cl or Br.

As used herein, recitations of "linear or branched" groups, such as linear or branched alkyl, are herein understood to include: groups that are linear (or "straight chain"), such as linear $C_1$-$C_{25}$ alkyl groups; and groups that are appropriately branched, such as branched $C_3$-$C_{25}$ alkyl groups.

The term "alkyl" as used herein means linear or branched, cyclic or acyclic $C_1$-$C_{25}$ alkyl. Linear or branched alkyl can include $C_1$-$C_{25}$ alkyl, such as $C_1$-$C_{20}$ alkyl, such as $C_2$-$C_{10}$ alkyl, such as $C_1$-$C_{12}$ alkyl, such as $C_1$-$C_6$ alkyl. Examples of alkyl groups from which the various alkyl groups of the present invention can be selected from, include, but are not limited to, those recited further herein. Alkyl groups can include "cycloalkyl" groups. The term "cycloalkyl" as used herein means groups that are appropriately cyclic, such as, but not limited to, $C_3$-$C_{12}$ cycloalkyl (including, but not limited to, cyclic $C_5$-$C_7$ alkyl, or cyclic $C_3$-$C_{10}$ alkyl) groups. Examples of cycloalkyl groups include, but are not limited to, those recited further herein. The term "cycloalkyl" as used herein also includes: bridged ring polycycloalkyl groups (or bridged ring polycyclic alkyl groups), such as, but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein means groups that are appropriately cyclic, such as, but not limited to, $C_2$-$C_{12}$ heterocycloalkyl groups, such as $C_5$-$C_7$ heterocycloalkyl groups, such as $C_2$-$C_{10}$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein also includes: bridged ring polycyclic heterocycloalkyl groups, such as, but not limited to, 7-oxabicyclo[2.2.1]heptanyl; and fused ring polycyclic heterocycloalkyl groups, such as, but not limited to, octahydrocyclopenta[b]pyranyl, and octahydro-1H-isochromenyl.

The term "heteroaryl", as used herein, includes, but is not limited to, $C_3$-$C_{18}$ heteroaryl, such as, but not limited to, $C_3$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, furanyl, pyranyl, pyridinyl, isoquinoline, and pyrimidinyl.

As used herein, the term "fused ring polycyclic-aryl-alkyl group" and similar terms such as, fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

The term "aralkyl", as used herein, includes, but is not limited to, $C_6$-$C_{24}$ aralkyl, such as, but not limited to, $C_6$-$C_{10}$ aralkyl, and means an alkyl group substituted with an aryl group. Examples of aralkyl groups include, but are not limited to, benzyl and phenethyl.

Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are not limited to, vinyl, allyl and propenyl. Representative alkynyl groups include, but are not limited to, ethynyl, 1-propynyl, 2-propynyl, 1-butyryl, and 2-butyryl. Representative cycloalkyl groups include, but are not limited to, cyclopropyl, cyclobutyl, cyclopentyl, cyclohexyl, and cyclooctyl substituents. Representative heterocycloalkyl groups include, but are not limited to, imidazolyl, tetrahydrofuranyl, tetrahydropyranyl and piperidinyl. Representative aryl groups include, but are not limited to, phenyl, naphthyl, anthracynyl, phenanthrenyl, and tetracenyl (including structural isomers thereof). Representative heteroaryl groups include, but are not limited to, furanyl, pyranyl, pyridinyl, isoquinolinyl, and pyrimidinyl. Representative aralkyl groups include, but are not limited to, benzyl and phenethyl.

The term "nitrogen-containing heterocycle", as used herein, includes, but is not limited to, a nitrogen-containing ring wherein the nitrogen-containing ring is bonded through a ring nitrogen. Examples of nitrogen-containing heterocycles include, but are not limited to, cyclic aminos, such as morpholino, piperidino, and pyrrolidino; and heteroaromatics, such as imidazole, pyrrole, indole, and carbazole.

As used herein, recitations of "substituted" group, means a group including, but not limited to, alkyl group, heterocycloalkyl group, aryl group, and/or heteroaryl group, in which at least one hydrogen thereof has been replaced or substituted with a group that is other than hydrogen, such as, but not limited to, alkoxy groups; halo groups (e.g., F, Cl, I, and Br); hydroxyl groups; thiol groups; alkylthio groups; arylthio groups; ketone groups; aldehyde groups; ester groups; carboxylic acid groups; phosphoric acid groups; phosphoric acid ester groups; sulfonic acid groups; sulfonic acid ester groups; nitro groups; cyano groups; alkyl groups (including aralkyl groups); alkenyl groups; alkynyl groups; haloalkyl groups; perhaloalkyl groups; heterocycloalkyl groups; aryl groups (including alkaryl groups, including hydroxyl substituted aryl, such as phenol, and including poly-fused-ring aryl); heteroaryl groups (including poly-fused-ring heteroaryl groups); amino groups, such as —$N(R^{11'})(R^{12'})$ where $R^{11'}$ and $R^{12'}$ are each independently selected, for example, from hydrogen, alkyl, heterocycloalkyl, aryl, or heteroaryl; carboxylate groups; siloxane groups; alkoxysilane groups; polysiloxane groups; amide groups; carbamate groups; carbonate groups; urea groups; polyester groups; polyether groups; polycarbonate groups; polyurethane groups; acrylate groups; methacrylate groups; nitrogen-containing heterocycles; or combinations thereof, including those classes and examples as described further herein.

As used herein, "at least one of" is synonymous with "one or more of", whether the elements are listed conjuctively or disjunctively. For example, the phrases "at least one of A, B, and C" and "at least one of A, B, or C" each mean any one of A, B, or C, or any combination of any two or more of A, B, or C. For example, A alone; or B alone; or C alone; or A and B; or A and C; or B and C; or all of A, B, and C.

As used herein, "selected from" is synonymous with "chosen from" whether the elements are listed conjunctively or disjunctively. Further, the phrases "selected from A, B, and C" and "selected from A, B, or C" each mean any one of A, B, or C, or any combination of any two or more of A, B, or C. For example, A alone; or B alone; or C alone; or A and B; or A and C; or B and C; or all of A, B, and C.

The discussion of the invention may describe certain features as being "particularly" or "preferably" within certain limitations (e.g., "preferably", "more preferably", or "even more preferably", within certain limitations). It is to be understood that the invention is not limited to these particular or preferred limitations but encompasses the entire scope of the disclosure.

The invention comprises, consists of, or consists essentially of, the following aspects of the invention, in any combination.

The photochromic compounds according to the present invention can be represented by one or more of the core skeletal structures described below. Each available numbered ring position (e.g., 1, 2, 5, 8, 9, 10, 11, and/or 12) of the core skeletal structure of Formula (I) can have covalently bonded thereto hydrogen or a group other than hydrogen, for example, such as a group described herein. Examples of such groups are described below.

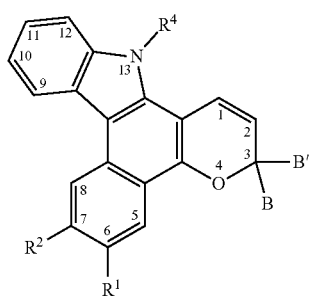

(I)

With reference to Formula (I), $R^1$ and $R^2$ are each independently substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, a nitrogen containing heterocycle, substituted or unsubstituted alkyl, substituted or unsubstituted aryl, —NHC(O)$R^a$, or —OC(O)$R^a$. Examples of groups from which $R^a$ can be selected include substituted or unsubstituted alkyl, substituted or unsubstituted aryl, substituted or unsubstituted heteroaryl, substituted or unsubstituted alkoxy, substituted or unsubstituted aryloxy, substituted or unsubstituted alkylthio, or substituted or unsubstituted arylthio. $R^4$ is selected from hydrogen, substituted or unsubstituted alkyl, substituted or unsubstituted heterocycloalkyl, allyl, substituted or unsubstituted aryl, or substituted or unsubstituted heteroaryl. For example, $R^4$ can be substituted or unsubstituted phenyl or substituted or unsubstituted alkyl. B and B' are each independently substituted or unsubstituted aryl, or substituted or unsubstituted heteroaryl. Each substituted aryl or substituted heteroaryl can be substituted with a group having a Hammett $\sigma_p$ value of greater than –0.50. The relative strength of electron donor groups is frequently described by Hammett Sigma values, or $\sigma_p$ values. A list of Hammett $\sigma_p$ values for various substituents can be found in "A Survey of Hammett Substituent Constants and Resonance and Field Parameters", C. Hansch, A. Leo, and R. W. Taft, *Chem. Rev.*, 1991, 91, 165-195, which disclosure is incorporated herein by reference. Non-limiting examples of suitable substituents having a Hammett $\sigma_p$ value of greater than –0.50 include halo groups (i.e., fluoro or bromo), alkyl, perhaloalkyl, phenyl, methyl, phenyl ether, aralkyl, ethoxy, methoxy, p-aminophenyl, arylthio, alkylthio, amide, carboxylate, aryl, heteroaryl, hydroxyl, cyano, or ester.

Examples of groups from which $R^1$ can be selected include, but are not limited to, substituted or unsubstituted alkoxy. Examples of groups from which $R^2$ can be selected include, but are not limited to, substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, or a nitrogen-containing heterocycle. B and B' can each independently be substituted aryl or substituted heteroaryl. Each substituted aryl or substituted heteroaryl can be substituted with a group having a Hammett $\sigma_p$ value of –0.5 to 0.8. B and B' can each independently be substituted or unsubstituted phenyl. Each phenyl substituent can be selected from alkoxy, halo, alkyl, or aryloxy. $R^1$ and $R^2$ taken together can form a cyclic structure, such as a ring structure.

Additionally or alternatively, the photochromic compounds of the present invention can be represented by the core skeletal structure of Formula (Ia):

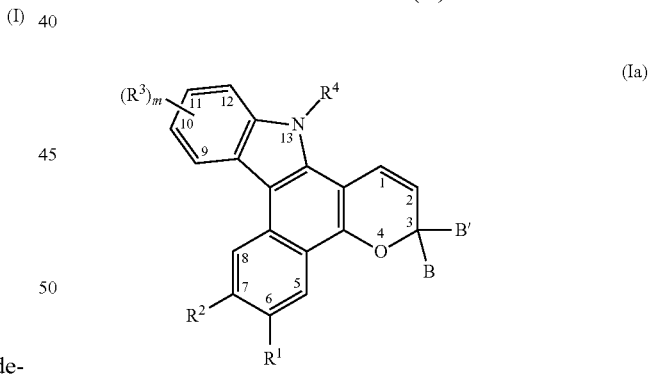

(Ia)

With reference to Formula (Ia), $R^1$, $R^2$, $R^4$, B and B' are as previously described with respect to Formula (I).

As described above, the remaining numbered ring positions (e.g., 1, 2, 5, and/or 8) of the core skeletal structure of Formula (Ia) without a specifically shown substituent can have covalently bonded thereto hydrogen or a group other than hydrogen, for example, such as a group described herein.

With further reference to Formula (Ia), m is 0 to 4, and $R^3$ independently for each m, is hydroxyl; cyano; (meth)acrylate; amino or nitrogen-containing heterocycle; a mesogen-containing group $L^1$; substituted or unsubstituted alkyl; substituted or unsubstituted alkenyl; substituted or unsubstituted alkynyl; a halo group; a perhalo group; boronic ester or boronic acid; polyether, polyester, polycarbonate, or polyurethane; substituted or unsubstituted aryl; substituted or unsubstituted heterocycloalkyl; substituted or unsubstituted heteroaryl; substituted or unsubstituted alkoxy or substituted or unsubstituted aryloxy; substituted or unsubstituted alkylthio or substituted or unsubstituted arylthio; ketone, aldehyde, ester, carboxylic acid, carboxylate, or amide; carbonate, carbamate, or urea; or siloxane, alkoxysilane, or polysiloxane. For example, $R^3$ can be cyano; a halo group; haloalkyl; perhaloalkyl; substituted or unsubstituted aryl; or substituted or unsubstituted heteroaryl. For example, $R^3$ can be at the 11-position. For example, $R^3$ can be at the 10-position and be a mesogen-containing group $L^1$.

With further reference to Formula (Ia), each mesogen-containing group $L^1$ can independently be represented by the following Formula (II),

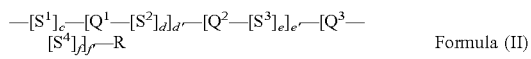

$Q^1$, $Q^2$, and $Q^3$ for each occurrence, are independently a divalent group selected from the group consisting of unsubstituted aryl, substituted aryl, unsubstituted cycloalkyl, and substituted cycloalkyl. The aryl substituents and cycloalkyl substituents can each independently be selected from the group consisting of liquid crystal mesogens, halogen, alkyl, alkoxy, alkylamino, dialkylamino, alkylthio, alkoxycarbonyl, alkylcarbonyl, alkoxycarbonyloxy, aryloxycarbonyloxy, perfluoroalkyl, and perfluoroalkoxy. With further reference to Formula (II), c, d, e, and f are each independently an integer of 0 to 3; and each $S^1$, $S^2$, $S^3$, and $S^4$ is independently chosen for each occurrence from a spacer unit selected from the group consisting of: (i) —C(Z)$_2$—, —N(Z)—, —C(Z)=C(Z)—, —C(Z)=N—, wherein Z for each occurrence is independently selected from the group consisting of hydrogen, alkyl, or aryl; (ii) —Si(CH$_3$)$_2$—, —Si(CH$_3$)$_2$O—; and (iii) —O—, —C(=O)—, —C≡C—, —N=N—, —S—, —S(=O)—, —(O=)S(=O)—, —(O=)S(=O)O—, —O(O=)S(=O)O—, provided that when two spacer units comprising heteroatoms are linked together the spacer units are linked so that heteroatoms are not directly linked to each other. With further reference to Formula (II), R is alkyl. With further reference to Formula (II), d', e' and f' are each independently 0, 1, 2, 3, and 4, provided that the sum of d'+e'+f' is at least 1.

As used herein, the term "polysiloxane" such as with regard to substituents of various groups of the photochromic compounds of the present invention, includes a material represented by the following Formula (G):

With reference to Formula (G), subscript t' is from 2 to 200, such as from 2 to 100, or 2 to 50, or from 2 to 25, or from 2 to 15, or from 2 to 10, or from 2 to 5, in each case inclusive of the recited values. With further reference to Formula (G): $R^{32}$ and $R^{33}$, for each t', are each independently selected from alkyl or aryl; and $R^{34}$ is selected from hydrogen, alkyl, or aryl. With some embodiments: $R^{32}$ and $R^{33}$ for each t', are each independently selected from methyl, ethyl, or phenyl; and $R^{34}$ is selected from hydrogen, methyl, ethyl, or phenyl.

As used herein, the term "polysiloxane" such as with regard to substituents of various groups of the photochromic compounds of the present invention, alternatively to or in addition to a material represented by Formula (G), includes a material represented by the following Formula (H):

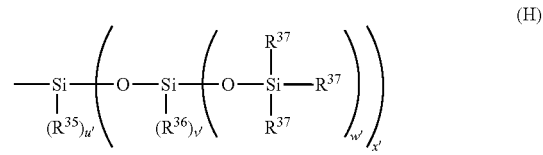

With reference to Formula (H), subscript u' is 0-2 and subscript x' is 1-3, provided that u'+x' is 3; and subscript v' is 0-2 and subscript w' is 1-3, provided that v'+w' is 3. With further reference to Formula (H), $R^{35}$ independently for each u', $R^{36}$ independently for each v' and each x', and each $R^{37}$ independently for each w' and each x', are in each case independently selected from alkyl (such as, but not limited to, methyl or ethyl) or aryl (such as, but not limited to, phenyl).

With some embodiments, the photochromic compounds of the present invention, such as those described with reference to Formulas (I) and/or (Ia) can each be used alone, or in combination with one or more other photochromic compounds. For example, the photochromic compounds of the present invention can be used in conjunction with one or more other photochromic compounds having activated absorption maxima within the range of 300 to 1,000 nanometers. Further, the photochromic compounds according to the present invention can be used in conjunction with one or more complementary conventional polymerizable or compatibilized photochromic compounds, such as for example, those disclosed in U.S. Pat. No. 6,113,814 (at col. 2, line 39 to col. 8, line 41), and U.S. Pat. No. 6,555,028 (at col. 2, line 65 to col. 12, line 56).

The photochromic compounds of the present invention can be used in combination with a mixture of other photochromic compounds. For example, although not limiting herein, mixtures of photochromic compounds can be used to attain certain activated colors, such as a near neutral gray or near neutral brown. See, for example, U.S. Pat. No. 5,645,767, col. 12, line 66 to col. 13, line 19, which describes the parameters that define neutral gray and brown colors.

Examples of classes of other photochromic compounds that can be used in combination with the photochromic compounds of the present invention, include, but are not limited to, indeno-fused naphthopyrans, naphtho[1,2-b]pyrans, naphtho[2,1-b]pyrans, spirofluoreno[1,2-b]pyrans, phenanthrenopyrans, quinolinopyrans, fluoroanthenopyrans, spiropyrans, benzoxazines, naphthoxazines, spiro(indoline) naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds, and mixtures thereof. Further examples of other photochromic compounds that can be used in combination with the photochromic compounds of the present invention include, but are not limited to, those disclosed at column 34, line 20 through column 35, line 13 of U.S. Pat. No. 9,028,728 B2.

The indolenaphthopyran compounds of the present invention can be prepared in accordance with art-recognized methods as follows. For purposes of non-limiting illustration and with reference to FIG. 1, general synthetic Scheme 1, the preparation of photochromic compounds according to the present invention is described as follows. Further detailed descriptions of the preparation of photochromic compounds of the present invention are provided further herein in the Examples. In FIG. 1, the various groups, such as $R^1$, $R^2$, $R^3$, $R^4$, B, B', $R_{aryl}$, and $R_{alkyl}$ of the various intermediates, reactants, and/or compounds depicted, are each as described herein, and/or represent precursors of such groups.

The synthesis of compounds depicted below as Formula III has been described in numerous references such as U.S. Pat. Nos. 6,296,785 or 7,262,295, with varying substituents.

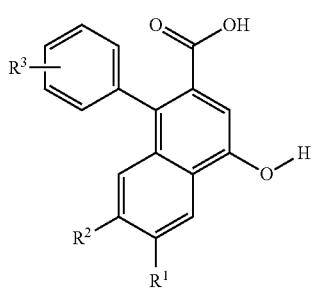

(III)

The hydroxyl group and the carboxylic acid group can be benzylated by reacting with benzyl chloride and a base such as sodium or potassium carbonate. The carboxylic ester that is formed can then be converted to the carboxylic acid by either acid or basic methods for ester hydrolysis. The resulting product is depicted below as Formula IIIa.

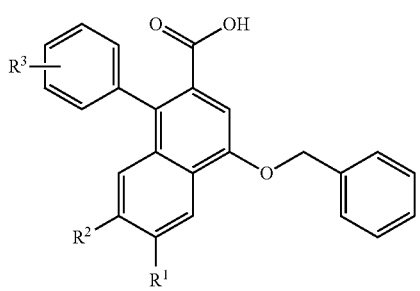

(IIIa)

The carboxylic acid group can then be converted to an $NH_2$ group via Curtius rearrangement conditions using diphenyl phosphorylazide which generates the isocyanate group followed by hydrolysis to yield the amine group, as depicted below in Formula IIIb.

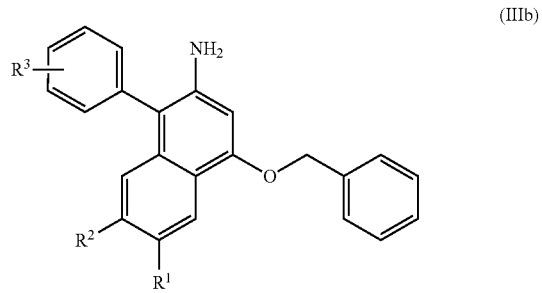

(IIIb)

The amine group is converted to an indole by first forming the picolinamide group by traditional amide forming reactions such as reacting the amine with acid chlorides, esters, or carboxylic acid groups. Reaction of the amine with picolinoyl chloride with a base such as triethylamine gives the picolinamide, as depicted in Formula IIIc, in high yields. The picolinamide can be cyclized to the indole, as depicted in Formula IIId, by use of a copper catalyst as described in Takumatso, K. et al. Org. Lett. 2014, 16, 2892. See reaction depicted below.

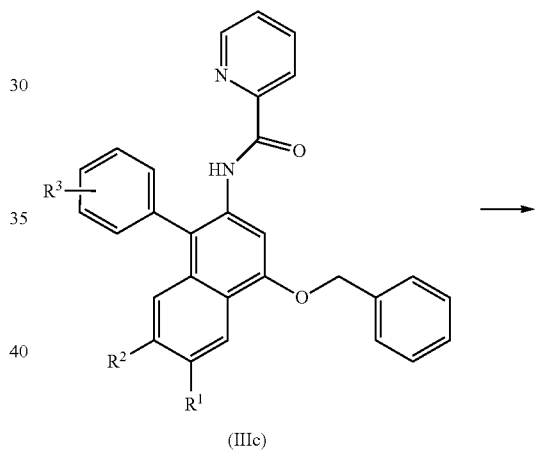

(IIIc)

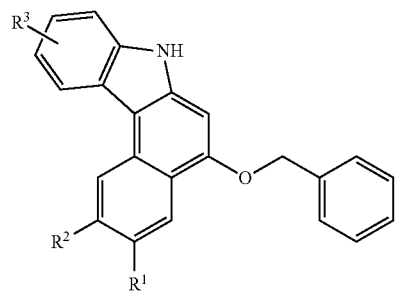

(IIId)

The indole ring as depicted in Formula IIId can also be formed by reacting the amine of Formula IIIb with Tosyl (Ts) chloride or anhydride to form a N-Ts group, as depicted in Formula IIIe. This group can be cyclized with palladium catalyst as described in Youn, S. W. Org. Lett. 2011, 13, 3738. See reaction depicted below.

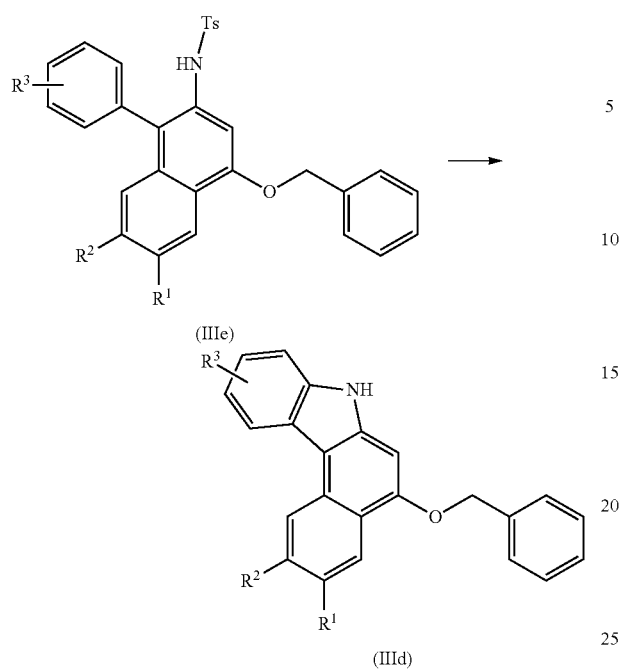

Alternatively, the amino group of Formula IIIb can be converted to an azide group, as depicted in Formula IIIf, by forming the diazonium salt under Sandmeyer conditions followed by displacement with a salt of azide such as sodium azide. The indole group of Formula IIId can then be formed by exposure to UV light in a solvent such as THF. See reaction depicted below.

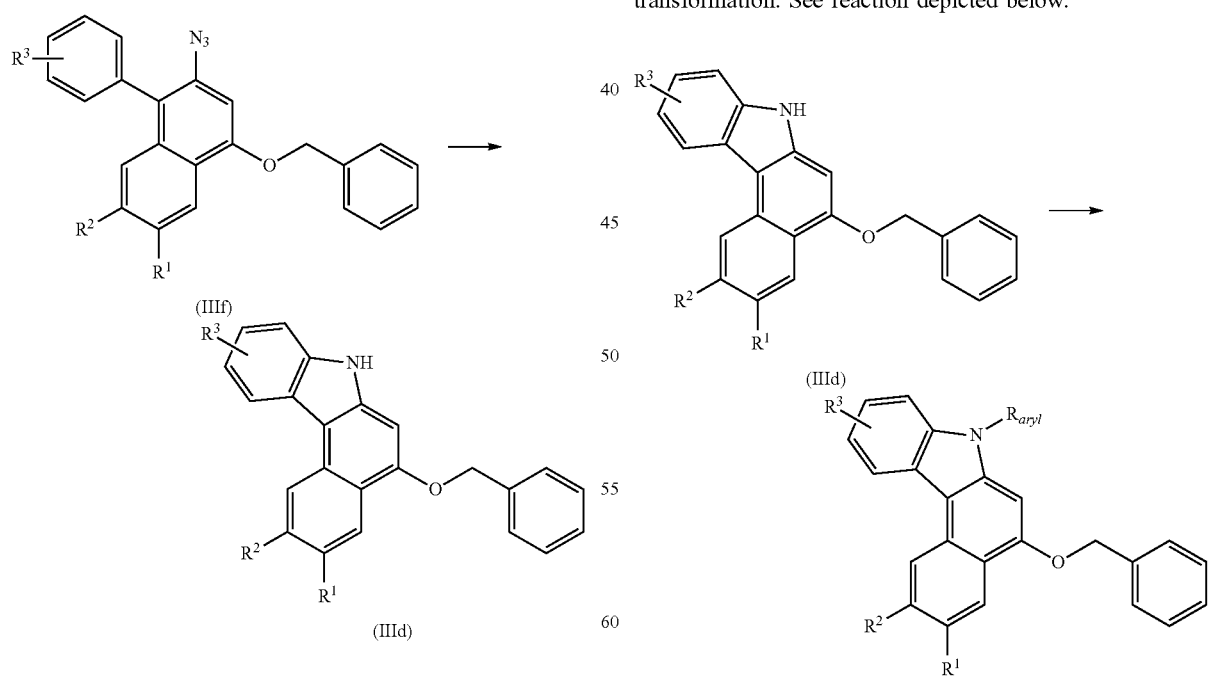

The alkylation of the indole group as depicted in Formula IIIg' can be accomplished by reaction with an alkyl halide, triflate, or tosylate in the presence of a base such as sodium or potassium terbutoxide. Alternatively the indole can be deprotonated by strong base such as sodium hydride or n-butyl lithium and then the anion reacted with the alkyl alkyl halide, triflate, or tosylate. See reaction depicted below.

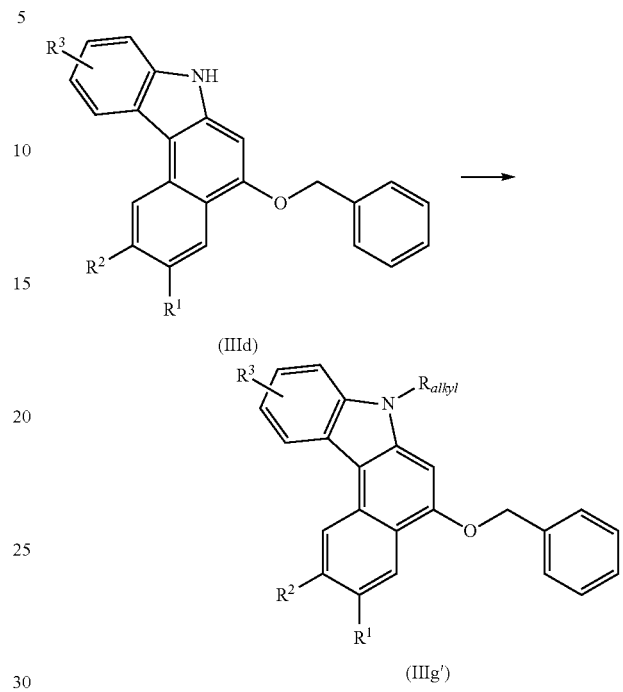

The indole group can be arylated, as depicted in Formula IIIg', by cross coupling reactions with transition metal catalysts and aryl halides. Ullmann coupling methodology with a copper catalyst is common method to perform this transformation. See reaction depicted below.

The indole can also be arylated as depicted in Formula IIIg' via nucleophilic aromatic substitution, such as by reaction with an aryl fluoride in a suitable solvent such as tetrahydrofuran or dimethylformamide.

The benzyl protecting group can be removed by palladium hydrogenation conditions or with a strong acid. See reaction depicted below, where Formula IIIg refers to an indole substituted with any $R^4$ as described herein, and the deprotected product is shown in Formula IIIh.

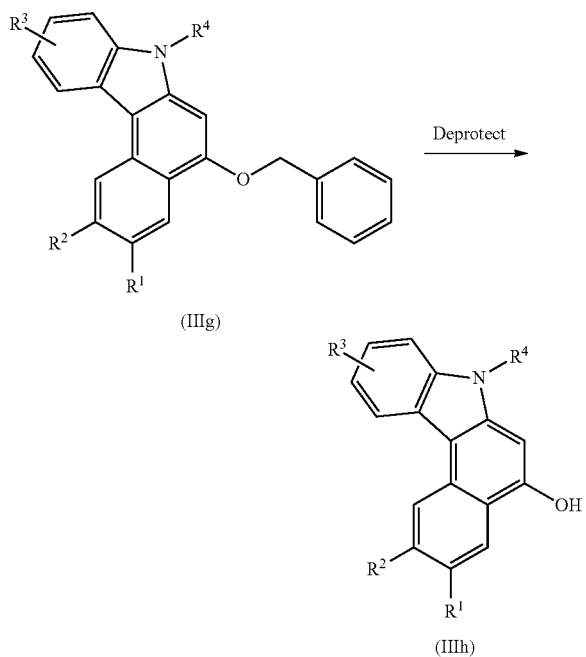

The indole-fused naphthol depicted in Formula IIIb can then be reacted with aryl propargyl alcohols under acidic conditions to yield indole-fused naphthopyrans, as depicted in Formula Ia. See reaction depicted below.

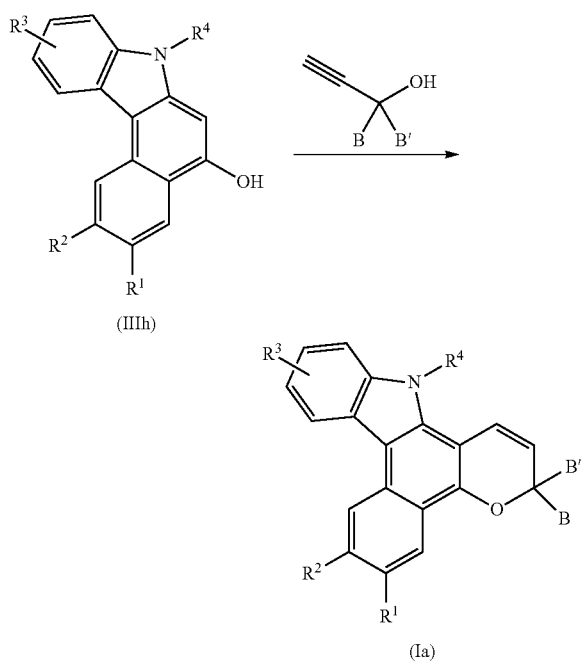

As previously mentioned and illustrated in the examples below, the compounds of the present invention exhibit A band to B band absorption ratios of greater than 3:1 and in some cases greater than 6:1, such as 3 to 7:1, such as 3 to 6.5:1, such as 3 to 6.4:1, or such as 3.45 to 6.4:1.

In accordance with the present invention there is also provided a photochromic composition, which includes at least one photochromic compound according to the present invention, such as those represented by Formula (I) or (Ia), as described previously herein.

The photochromic composition can include: (i) an organic material, in which the organic material is at least one of a polymeric material, an oligomeric material, or a monomeric material; and (ii) a photochromic compound according to the present invention, which is incorporated into at least a portion of the organic material. The photochromic compound can be incorporated into a portion of the organic material by methods including, but not limited to, at least one of blending or bonding the photochromic compound with the organic material or a precursor of the organic material. As used herein with reference to the incorporation of photochromic compounds into an organic material, the terms "blending" and "blended" mean that the photochromic compound/material is intermixed or intermingled with the at least a portion of the organic material, but not bonded to the organic material. Further, as used herein with reference to the incorporation of photochromic compounds into an organic material, the terms "bonding" or "bonded" mean that the photochromic compound/material is linked, such as by one or more covalent bonds, to a portion of the organic material or a precursor thereof. For example, although not limiting herein, the photochromic material can be linked to the organic material through a reactive substituent.

When the organic material is a polymeric material, the photochromic compound can be incorporated into at least a portion of the polymeric material or at least a portion of the monomeric material or oligomeric material from which the polymeric material is formed. For example, photochromic compound(s) according to the present invention that have a reactive substituent can be bonded to an organic material such as a monomer, oligomer, or polymer having a group with which a reactive moiety may be reacted, or the reactive moiety can be reacted as a co-monomer in the polymerization reaction from which the organic material is formed, for example, in a co-polymerization process.

As discussed above, the photochromic compositions according to present invention can include an organic material chosen from a polymeric material, an oligomeric material and/or a monomeric material, with some embodiments. Examples of polymeric materials that can be used with the photochromic compositions of the present invention include, but are not limited to: poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl (meth)acrylamide functional polymers; poly(siloxane); poly(silane); and combinations and mixtures thereof. Further classes and examples of polymeric materials that can be used with the photochromic compositions of the present invention include, but are not limited to, those disclosed at column 39, line 45 through column 40, line 67 of U.S. Pat. No. 9,028,728 B2.

The photochromic composition of the present invention can include at least one of, a complementary photochromic material (including one or more of those other photochromic materials and compounds described previously herein), a photoinitiator, a thermal initiator, a polymerization inhibitor, a solvent, a light stabilizer, a heat stabilizer, a mold release agent, a rheology control agent, a leveling agent, a free radical scavenger, and/or an adhesion promoter.

The photochromic composition according to the present invention can be a photochromic coating composition. Photochromic coating compositions of the present invention can include: a photochromic compound according to the present invention, such as described previously herein with regard to Formulas (I) and/or (Ia); a resin composition that is optionally curable; and optionally a solvent. The photochromic coating composition can be in the form of art-recognized liquid coatings and powder coatings. The photochromic coating compositions of the present invention can be thermoplastic or thermosetting coating compositions. The photochromic coating composition can be a curable or thermosetting coating composition.

The curable resin composition of the curable photochromic coating compositions according to the present invention can include: a first reactant (or component) having functional groups, e.g., an epoxide functional polymer reactant; and a second reactant (or component) that is a crosslinking agent having functional groups that are reactive towards and that can form covalent bonds with the functional groups of the first reactant. The first and second reactants of the curable resin composition of the curable photochromic coating composition can each independently include one or more functional species, and are each present in amounts sufficient to provide cured photochromic coatings having a desirable combination of physical properties, e.g., smoothness, optical clarity, solvent resistance, and hardness.

Examples of curable resin compositions that can be used with the curable photochromic coating compositions according to the present invention include, but are not limited to: curable resin compositions including epoxide functional polymer (e.g., (meth)acrylic polymers containing residues of glycidyl (meth)acrylate) and epoxide reactive crosslinking agent (e.g., containing active hydrogens, such as hydroxyls, thiols and amines); and curable resin compositions including active hydrogen functional polymer (e.g., hydroxy, thiol, and/or amine functional polymer) and capped (or blocked) isocyanate functional crosslinking agent. By "capped (or blocked) isocyanate functional crosslinking agent" is meant a crosslinking agent having two or more capped isocyanate groups that can decap (or deblock) under cure conditions (e.g., at elevated temperature) to form free isocyanate groups and free capping groups. The free isocyanate groups formed by decapping of the crosslinking agent are preferably capable of reacting and forming substantially permanent covalent bonds with the active hydrogen groups of the active hydrogen functional polymer (e.g., with the hydroxy groups of a hydroxy functional polymer). Further examples of curable resin compositions that can be used with the curable photochromic coating compositions according to the present invention include, but are not limited to, those disclosed in: paragraphs [0176] through [0190] of WO 2016/142496 A1; and paragraphs [0005], [0037] through [0051], [0056] through [0059], and [0063] through [0065] of WO 2017/030545 A1.

Curable photochromic coating compositions according to the present invention can, optionally, contain additives such as waxes for flow and wetting, flow control agents, e.g., poly(2-ethylhexyl)acrylate, adjuvant resin to modify and optimize coating properties, antioxidants and ultraviolet (UV) light absorbers. Examples of useful antioxidants and UV light absorbers include those available commercially from BASF under the trademarks IRGANOX and TINUVIN. These optional additives, when used, are typically present in amounts up to 20 percent by weight (e.g., from 0.5 to 10 percent by weight), based on total weight of resin solids of the curable resin composition.

Photochromic compositions, photochromic articles and photochromic coating compositions according to the present invention can further include art-recognized additives that aid or assist in the processing and/or performance of the compositions or articles. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The photochromic compounds of the present invention can be used in amounts (or ratios) such that the compositions, organic material or substrate (e.g., photochromic articles and photochromic coatings) into which the photochromic compounds are incorporated or otherwise connected exhibits desired optical properties. The amount and types of photochromic material can be selected such that the composition, organic material or substrate is clear or colorless when the photochromic compound is in the closed-form (e.g., in the bleached or unactivated state), and can exhibit a desired resultant color when the photochromic compound (such as a photochromic indolenaphthopyran of the present invention) is in the open-form (e.g., when activated by actinic radiation). The precise amount of the photochromic material that is utilized in the various photochromic compositions and articles described herein is not critical provided that a sufficient amount is used to produce the desired effect. The particular amount of the photochromic material used can depend on a variety of factors, such as but not limited to, the absorption characteristics of the photochromic compound, the color and intensity of the color desired upon activation, and the method used to incorporate or connect the photochromic material to the substrate. Photochromic compositions according to the present invention can include the photochromic compound according to the present invention, including the compounds represented by Formula (I) or (Ia), in an amount of from 0.01 to 40 weight percent, such as from 0.05 to 15 weight percent, such as from 0.1 to 5 weight percent, based on the weight of the photochromic composition. For purposes of further non-limiting illustration, the amount of the photochromic compound/material including the compounds represented by Formula (I) or (Ia) that is incorporated into an organic material can range from 0.01 to 40 weight percent, such as from 0.05 to 15 weight percent, such as from 0.1 to 5 weight percent, based on the weight of the organic material.

The present invention also relates to photochromic articles that include one or more photochromic compounds according to the present invention, such as represented by Formula (I) or (Ia). The photochromic articles can be prepared by art-recognized methods, such as by imbibition methods, cast-in-place methods, coating methods, in-mold coating methods, over-mold methods, and lamination methods.

For example, the photochromic articles can be selected from ophthalmic articles, display articles, windows, mirrors, active liquid crystal cell articles, and passive liquid crystal cell articles.

For example, the photochromic articles of the present invention can be ophthalmic articles, and the ophthalmic articles can be selected from corrective lenses, non-corrective lenses, contact lenses, intra-ocular lenses, magnifying lenses, protective lenses, and visors.

For example, the photochromic articles of the present invention can be display articles, and the display articles can be selected from screens, monitors, and security elements.

Such photochromic articles, e.g., photochromic lenses, can transition from a first unactivated state (e.g., clear and non-blue blocking state) to a second activated state (e.g., colored and blue-blocking state) upon exposure to actinic radiation. The articles revert back to the first unactivated (and clear) state upon removal of the actinic radiation source. Thus, the photochromic articles according to the present invention provide enhanced protection from health risks associated with blue light exposure during outdoor activity, while maintaining acceptable aesthetics indoors.

The present invention is more particularly described in the following examples, which are intended as illustrative only, since numerous modifications and variations therein will be apparent to those skilled in the art.

EXAMPLES

The following examples are provided to illustrate photochromic compounds of the invention, particularly the improved color and durability of photochromic compounds of the invention. Part 1 provides descriptions of the synthesis of photochromic compounds of the invention. Part 2 provides an evaluation of the photochromic performance of the photochromic compounds of the invention versus comparative photochromic compounds.

Part 1: Synthesis of Photochromic Compounds

Example 1

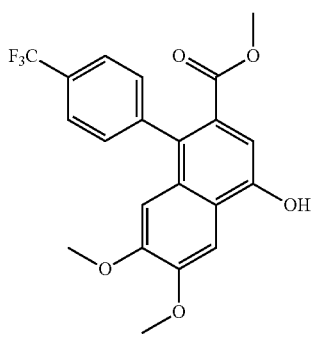 [SMILES: COC(=O)c1cc(O)c2cc(OC)c(OC)cc2c1-c1ccc(C(F)(F)F)cc1]

Step 1

Methyl 4-acetoxy-6,7-dimethoxy-1-(4-(trifluoromethyl)phenyl)-2-naphthoate (50 g, 131 mmol) was dispersed in methanol (200 ml) with stirring. Concentrated hydrochloric acid (8 ml) was added and the reaction mixture was heated to reflux for 4 hours. Once cool, the reaction mixture was concentrated to half the original volume and the product precipitated upon standing. The product was collected and dried under vacuum to give 41 g (90% yield) of a colorless powder.

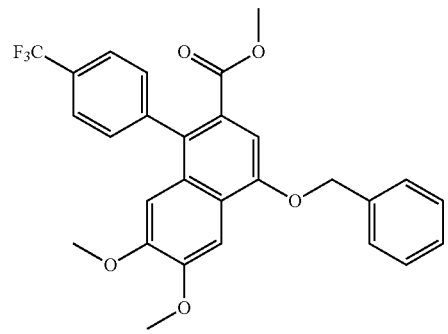 [SMILES: COC(=O)c1cc(OCc2ccccc2)c2cc(OC)c(OC)cc2c1-c1ccc(C(F)(F)F)cc1]

Step 2

While stirring under nitrogen, the product from Step 1 (41 g, 101 mmol) was dissolved in anhydrous dimethylformamide (200 ml) and potassium carbonate (28.0 g, 202 mmol) was added followed by benzyl chloride (15.3 g, 121 mmol). The reaction mixture was heated to 70° C. for 5 hours and let stir overnight at room temperature. A precipitate began to form and the reaction mixture was poured into ice water (1.0 L) with stirring. The precipitate was collected and dried under vacuum to give 49.44 g (99% yield) of a colorless solid.

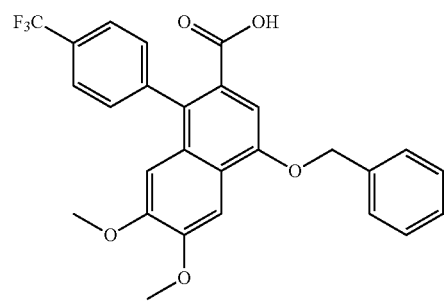 [SMILES: COc1cc2c(OCc3ccccc3)cc(C(=O)O)c(-c3ccc(C(F)(F)F)cc3)c2cc1OC]

Step 3

The product from Step 2 (49.4 g, 99.5 mmol) was suspended in 2-propanol (150 ml) with stirring. Sodium hydroxide solution (10% w/w in water, 150 ml) was added and the reaction mixture was heated to reflux for 16 hours. Once cool, the reaction mixture was poured into ice water (1.0 L) to form a colorless precipitate. The powder was collected and dried under vacuum to give 46.71 g (97% yield).

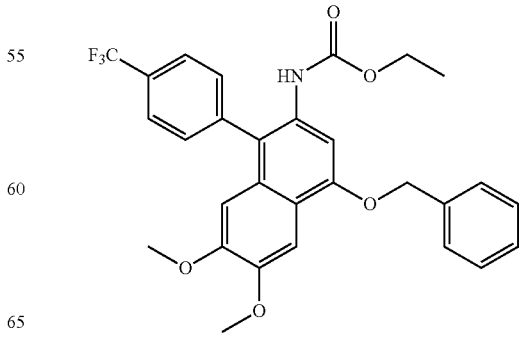

Step 4

While stirring under nitrogen, the product from Step 3 (46.7 g, 96.8 mmol) was suspended in anhydrous toluene (300 ml). Triethylamine (25.5 g, 252 mmol) and absolute ethanol (25 ml) were added dissolving the suspension. Diphenylphosphoryl azide (40 g, 145 mmol) was added portion-wise and the reaction was heated to reflux for 3 hours. Once cool, the reaction mixture was taken up in 200 ml of ethyl acetate, washed with water (4×300 ml), dried with sodium sulfate and concentrated under reduced pressure to give an off-white solid (50 g, 98% yield).

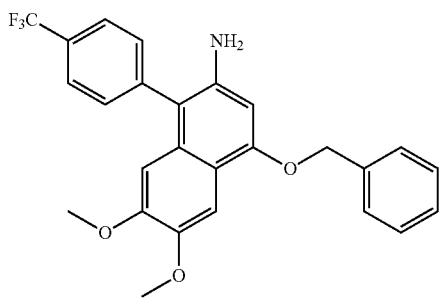 [SMILES: COc1cc2c(OCc3ccccc3)cc(N)c(-c3ccc(C(F)(F)F)cc3)c2cc1OC]

Step 5

The product from Step 4 (50.0 g, 95.1 mmol) was dispersed in a solution of ethanol (200 ml) and water (220 ml) with sodium hydroxide (19.2 g, 48.0 mmol) with stirring. The reaction mixture was heated to reflux for 4 hours. Once cool, the reaction mixture was poured into ice water (1.0 L) and a colorless precipitate was formed. The powder was collected and dried under vacuum to give 41.81 g (97% yield).

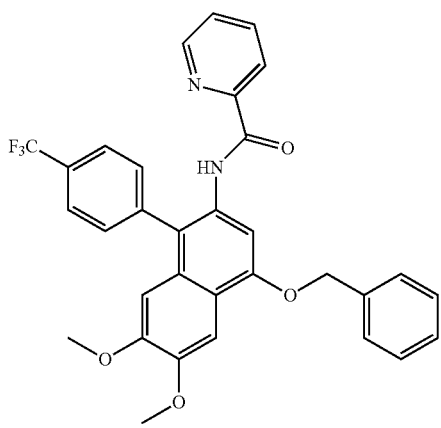 [SMILES: COc1cc2c(OCc3ccccc3)cc(NC(=O)c3ccccn3)c(-c3ccc(C(F)(F)F)cc3)c2cc1OC]

Step 6

While stirring under nitrogen, the product from Step 5 (41.81 g, 92.2 mmol) was taken up in dichloromethane (250 ml). Picolinic acid (17.0 g, 138.3 mmol) and 4-(dimethylamino)pyridine (1.13 g, 9.20 mmol) were added followed by N,N'-dicyclohexylcarbodiimide (22.8 g, 110.6 mmol). The reaction mixture was allowed to stir at room temperature for 4 hours. The reaction mixture was filtered and concentrated under reduced pressure to give a reddish solid. The material was washed with methanol, collected and dried under vacuum to give 50.9 g, (99% yield) of an off-white powder.

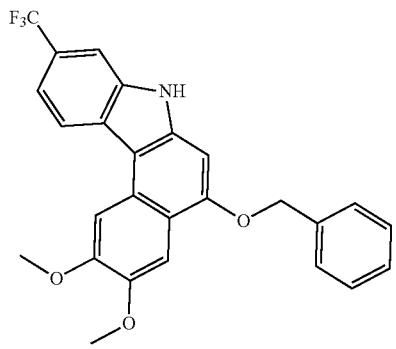 [SMILES: COc1cc2c(OCc3ccccc3)cc3[nH]c4cc(C(F)(F)F)ccc4c3c2cc1OC]

Step 7

While stirring under nitrogen, the product from Step 6 (50.9 g, 91.1 mmol) was dissolved in anhydrous dimethylformamaide (100 ml) and to this was added copper (II) acetate (33.1 g, 182.2 mmol) and glacial acetic acid (5.47 g, 91.1 mmol). The reaction mixture was heated to 150° C. for 20 hours to give 66% conversion of the starting material to product determined by high performance liquid chromatography. The reaction mixture was filtered over a celite pad and the pad was washed with 500 ml of ethyl acetate. The filtrate was added to reparatory funnel with water (1.0 L) containing ethylenediamine (10 ml) and the layers were separated. The organic layer was washed with water (3×300 ml), dried with sodium sulfate and concentrated under reduced pressure to give an off-white solid. The material was subjected to a second iteration of the reaction conditions and same isolation procedures. The resulting solid was washed twice with methanol (300 ml) to give an off-white powder (37.44 g 91% yield). The product indole core, 5-(benzyloxy)-2,3-dimethoxy-9-(trifluoromethyl)-7H-benzo[c]carbazole, was confirmed by $^1$H NMR and mass spectroscopy.

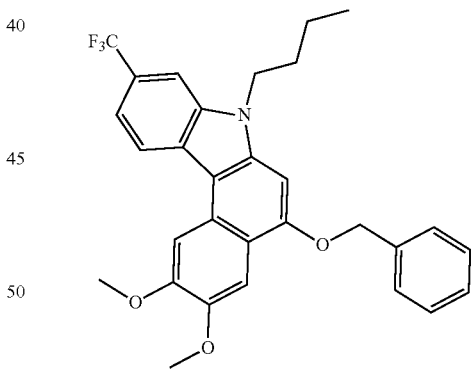

Step 8

While stirring under nitrogen, the indole core from Step 7 (5.0 g, 11.1 mmol) was dissolved in anhydrous dimethylformamide (40 ml) and sodium hydride (0.8 g, 33.2 mmol) was added slowly. After 15 minutes, iodobutane (2.25 g, 12.2 mmol) was added and the reaction mixture was stirred at room temperature for 30 minutes. The reaction mixture was taken up in ethyl acetate (200 ml) and washed with water (3×200 ml). The organic layer was dried with sodium sulfate and concentrated under reduced pressure onto silica gel. Chromatography (silica gel, 0-50% dichloromethane in hexanes) yielded the product as a colorless solid (3.4 g, 60% yield).

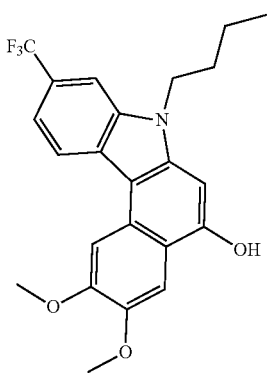 [SMILES: CCCCn1c2cc(C(F)(F)F)ccc2c2c3cc(OC)c(OC)cc3c(O)cc21]

Step 9

While stirring under nitrogen, the product from Step 8 (1.50 g, 3.0 mmol) was combined with ammonium formate (0.75 g, 11.84 mmol) and palladium on carbon (Degussa type E1003 U/W, 0.09 g, 0.9 mmol) in dimethylformamide (20 ml). The reaction mixture was heated to 85° C. for 2 hours. Once cool, the reaction mixture was filtered over a pad of celite and the pad was washed with ethyl acetate (250 ml). The filtrate was washed with water (3×300 ml), dried with sodium sulfate and concentrated under reduced pressure to give an off-white solid that was used without further purification.

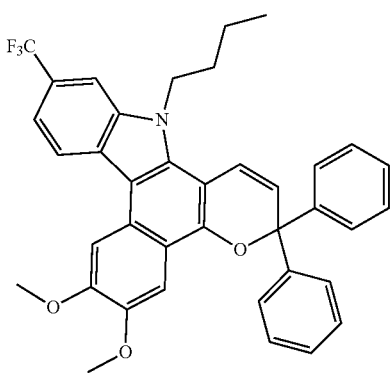 [SMILES: CCCCn1c2cc(C(F)(F)F)ccc2c2c3cc(OC)c(OC)cc3c3c(c21)C=CC(c1ccccc1)(c1ccccc1)O3]

Step 10

While stirring under nitrogen, the product from Step 9 (0.62 g, 1.48 mmol) was combined with 1,1-diphenylprop-2-yn-1-ol (0.37 g, 1.78 mmol) in toluene (25 ml) and heated to 75° C. p-Toluenesulfonic acid (5-10 mg) was added and the reaction mixture was heated to reflux for 2 hours. Once cool the reaction mixture was taken up in ethyl acetate (25 ml), washed with saturated sodium bicarbonate solution (25 ml) and water (2×50 ml). The organic layer was dried with sodium sulfate and concentrated under reduced pressure to give a dark oil. The product was recrystallized twice from methyl tert-butylether, tetrahydrofuran and methanol to give Example 1 as a light yellow powder (0.48 g, 54% yield) and confirmed by mass spectrometry.

Example 2

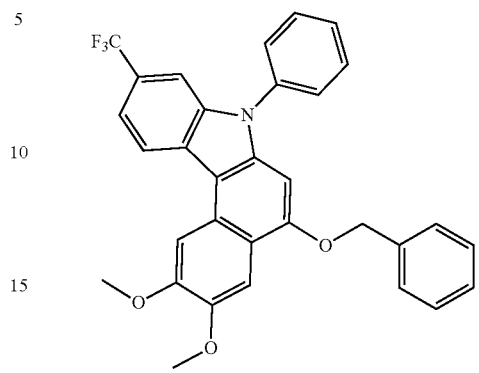

Step 1

While stirring under nitrogen, the indole core prepared in Example 1, Step 7 (3.0 g, 6.64 mmol) was combined with bromobenzene (4.2 g, 26.6 mmol), copper iodide (0.63 g, 3.32 mmol), potassium carbonate (1.82 g, 13.2 mmol), 1,10-phenanthroline (0.24 g, 1.30 mmol) and dibenzo-18-crown-6-ether (0.24 g, 0.70 mmol) in anhydrous dimethylformamide (30 ml). The reaction mixture was heated to 150° C. for 5 hours. Once cool, the reaction mixture was taken up in ethyl acetate (250 ml) and washed initially with water (200 ml) with ethylene diamine (10 ml) followed by water (2×250 ml). The organic layer was dried with sodium sulfate and concentrated under reduced pressure to give a brown solid. The product was recrystallized twice from methyl-tert-butylether, tetrahydrofuran and methanol to give an off-white powder (3.20 g, 91% yield).

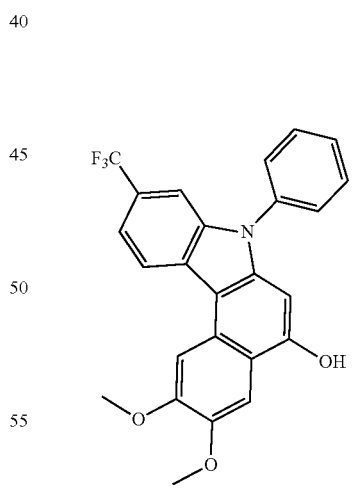

Step 2

The product from Step 1 (1.20 g, 2.27 mmol) was treated to the conditions of Example 1, Step 9 to give an off-white solid that was used without further purification.

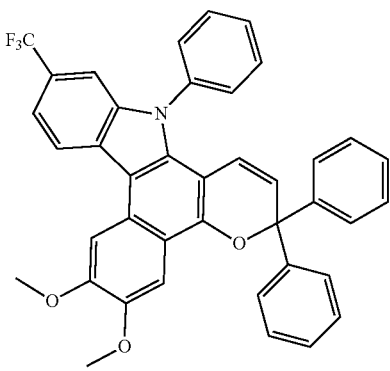 [SMILES: COc1cc2c3c(c4c(c2cc1OC)c1ccc(C(F)(F)F)cc1n4-c1ccccc1)C=CC(c1ccccc1)(c1ccccc1)O3]

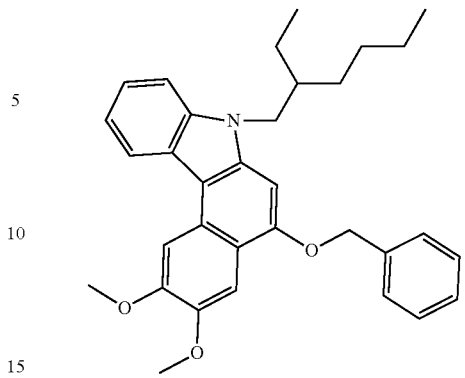

Step 3

The product from Step 2 was treated to conditions of Example 1, Step 10 to give a little yellow powder (1.12 g, 79% yield) that was confirmed by mass spectrometry.

Examples 3-7

Additional photochromic dyes were prepared according to Example 2 and are summarized in Table 1. For each example, an appropriate substituted phenyl bromide was used in place of bromobenzene in Example 2, Step 1 indicated in the N-Coupling Component column in Table 1. As well an appropriate substituted 1,1-diphenylprop-2-yn-1-ol ("propargyl alcohol") was used in Example 2, Step 3 indicated in the Propargyl Alcohol column in Table 1. The products were characterized by mass spectrometry.

Examples 8-10

Additional photochromic dyes were prepared as shown in Table 1, which were aminated in the 7-position. The amination reaction was performed as follows: While stirring under nitrogen, the Amination Component shown in Table 2 (2.90 mmol) was added to anhydrous tetrahydrofuran (35 ml). n-Butyllithium (2.5M in hexanes, 1.2 ml) was added slowly and the mixture was allowed to stir at room temperature for 5 minutes. The Starting Indolenaphthopyran Component listed in Table 2 (0.71 mmol) was added and the reaction mixture was allowed to stir for an additional 4 hours. The reaction mixture was poured into water (250 ml) and extracted with ethyl acetate (2×50 ml). The organic layers were dried with sodium sulfate and concentrated onto silica gel. Chromatography (silica gel, 0 to 50% dichloromethane in hexanes) yielded the product as an off-white solid that was confirmed by mass spectrometry.

Example 11-13

Additional photochromic dyes were prepared according to conditions of Example 1 and 2 except that methyl 4-acetoxy-6,7-dimethoxy-1-(4-(trifluoromethyl)phenyl)-2-naphthoate of Example 1, Step 1 was replaced with methyl 4-acetoxy-6,7-dimethoxy-1-phenyl-2-naphthoate. The reactions are summarized in Table 1 and the different core is indicated in the Indole Core column. The products were characterized by mass spectrometry.

Step 1

The indole core, 5-(benzyloxy)-2,3-dimethoxy-7H-benzo[c]carbazole, was treated to conditions of Example 1, Step 8 with 1-bromo-2-ethylhexane instead of iodobutane. The results are summarized in Table 1.

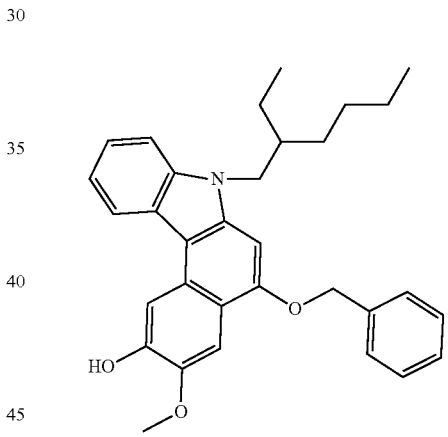

Step 2

While stirring under nitrogen, a methyl Grignard solution (1.4 M, 29.0 ml) was added slowly by syringe to dimethylpiperidine (4.93 g, 40.0 mmol) and the reaction mixture was allowed to stir for 10 minutes. The product from Step 1 (4.95 g, 10.0 mmol) was dissolved in anhydrous tetrahydrofuran (30 ml) and added dropwise over 10 minutes to the Grignard/dimethylpiperdine mixture. Once added, the reaction mixture was refluxed for 3 hours. Upon cooling, the reaction mixture as poured into a 1M HCl solution (75 ml) and the aqueous layer was extracted with ethyl acetate (3×150 ml). The organic layers were combined, dried with sodium sulfate and concentrated under reduced pressure onto silica. Chromatography (silica gel, 0-100% dichloromethane in hexanes) yielded an semi-solid (2.17 g, 44% yield).

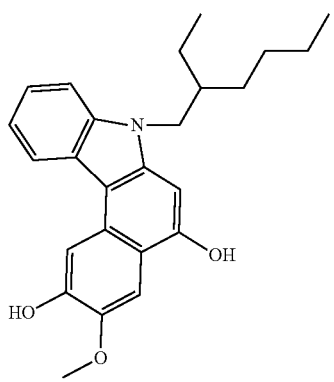 [SMILES: CCCCC(CC)Cn1c2ccccc2c2c3cc(O)c(OC)cc3c(O)cc21]

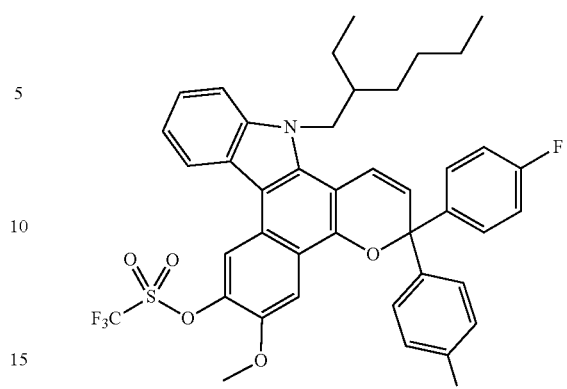

Step 3

The product of Step 2 (2.17 g, 4.50 mmol) was treated to the conditions of Example 1, Step 9 to give a foam that was used without further purification.

Step 5

While stirring under nitrogen, the product of Step 4 (0.85 g, 1.38 mmol) was dissolved in anhydrous dichloromethane (25 ml). Anhydrous pyridine (0.5 ml, 5.52 mmol) was added and the reaction mixture was cooled in an ice bath. Trifluoromethanesulfonic anhydride (0.51 g, 1.80 mmol) was added dropwise. After 30 minutes the reaction mixture was poured into water and the layers were separated. The aqueous layer was washed with dichloromethane (2×30 ml). The organic layers were combined, dried with sodium sulfate and concentrated under reduced pressure to give a brown/green glass (1.0 g, 97% yield).

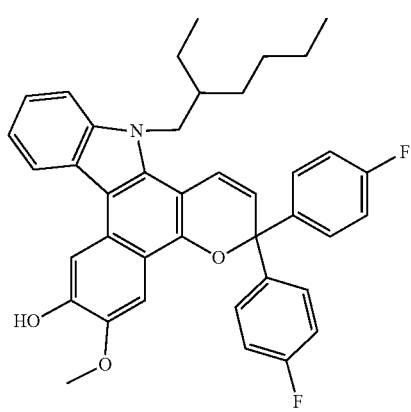 [SMILES: CCCCC(CC)Cn1c2ccccc2c2c3cc(O)c(OC)cc3c3c(c21)C=CC(c1ccc(F)cc1)(c1ccc(F)cc1)O3]

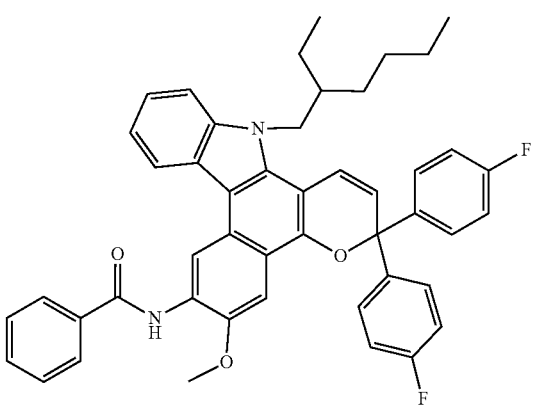 [SMILES: CCCCC(CC)Cn1c2ccccc2c2c3cc(NC(=O)c4ccccc4)c(OC)cc3c3c(c21)C=CC(c1ccc(F)cc1)(c1ccc(F)cc1)O3]

Step 4

While stirring under nitrogen, the product of Step 3 was combined with 1,1-bis(4-fluorophenyl)prop-2-yn-1-ol and dissolved in toluene (40 ml). The mixture was heated towards reflux and p-toluenesulfonic acid (10 mg) was added. The reaction mixture was heated at reflux for 5 hours until the conversion of the reaction was determined to be 60% by high performance liquid chromatography and once cool, concentrated onto silica gel. Chromatography (silica gel, 5-50% ethyl acetate in hexanes) yielded a brown/green glass (0.85 g, 30% yield).

Step 6

The product from Step 5 (1.0 g, 1.33 mmol) was combined with benzamide (0.25 g, 2.0 mmol), cesium carbonate (1.80 g, 5.52 mmol) and 4,5-bis(diphenylphosphino)-9,9-dimethylxanthene (Xantphos) in toluene and ethanol solution (30 ml, 9:1 v/v) and sparged under nitrogen for 10 minutes. Tris(dibenzylideneacetone)dipalladium(0) (0.12 g, 0.13 mmol) was added and the reaction mixture was heated to reflux for 2 hours. The reaction mixture was taken up in ethyl acetate (100 ml), washed with water (2×100 ml), dried with sodium sulfate and concentrated onto silica gel. Chromatography (silica gel, 0-30% ethyl acetate in hexanes) yielded a brown solid. Recrystallization from methanol gave 0.38 g (40% yield) of a light yellow powder that was confirmed by mass spectrometry.

Example 15

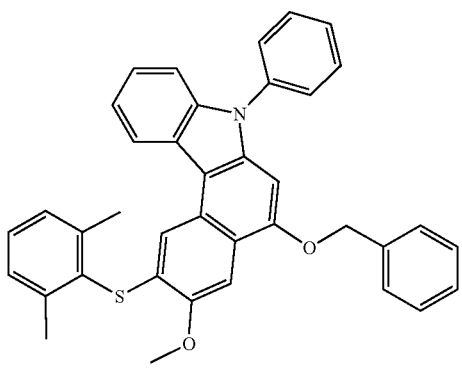 [SMILES: COc1cc2c(OCc3ccccc3)cc3c(c2cc1Sc1c(C)cccc1C)c1ccccc1n3-c1ccccc1]

Step 1

The initial intermediate was prepared according to the conditions of Example 1 and 2 except that methyl 4-acetoxy-6,7-dimethoxy-1-(4-(trifluoromethyl)phenyl)-2-naphthoate was replaced by methyl 4-acetoxy-7-((2,6-diemthylphenyl)thio)-6-methoxy-1-phenyl-2-naphthoate and summarized in Table 1.

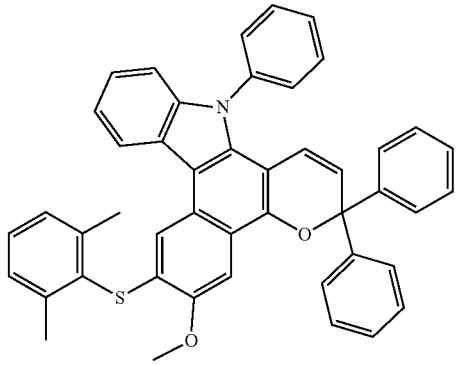 [SMILES: COc1cc2c3c(c4c(c2cc1Sc1c(C)cccc1C)c1ccccc1n4-c1ccccc1)C=CC(c1ccccc1)(c1ccccc1)O3]

Step 2

While stirring under nitrogen, the product of Step 1 (1.46 g, 2.58 mmol) was combined with p-toluenesulfonic acid (0.45 g, 2.58 mmol) in toluene (30 ml) and heated to 85° C. for 1 hour. Once cool, the reaction mixture was washed with water (2×75 ml), dried with sodium sulfate and concentrated under reduced pressure to give a yellow solid (1:2 mixture of product to byproduct). The solid was suspended in toluene (20 ml) and 1,1-diphenylprop-2-yn-1-ol (0.36 g, 1.73 mmol) was added. The reaction mixture was heated towards reflux and p-toluenesulfonic acid (5-10 mg) was added. After heating the reaction mixture at reflux for 1 hour, the reaction mixture was let cool and concentrated under reduced pressure onto silica gel. Chromatography (silica gel, 0-50% dichloromethane in hexanes) yielded a yellow solid. Recrystallization from methyl tert-butylether, tetrahydrofuran and methanol gave a light yellow powder (0.23 g, 44% yield based on mixture) that was confirmed by mass spectroscopy.

Comparative Examples CE1-CE5

Comparative indole photochromic examples were prepared in similar fashion and are summarized in Table 1. The products were characterized by mass spectrometry.

TABLE 1

| Ex. # | Structure | Indole Core | N-Coupling component | Yield¹ (%) | Propargyl Alcohol | Yield² (%) |
|---|---|---|---|---|---|---|
| 1 | 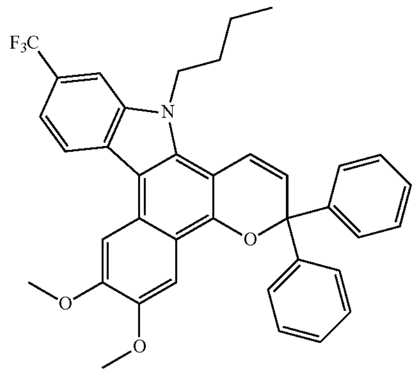 [SMILES: CCCCn1c2cc(C(F)(F)F)ccc2c2c3cc(OC)c(OC)cc3c3c(c21)C=CC(c1ccccc1)(c1ccccc1)O3] | | n-butyl bromide | 60 | 1,1-diphenyl-2-propyn-1-ol | 54 |
| 2 | 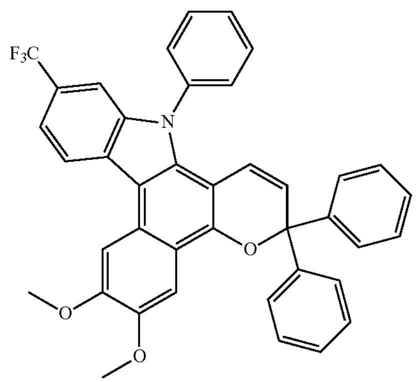 [SMILES: COc1cc2c3c(c4c(c2cc1OC)c1ccc(C(F)(F)F)cc1n4-c1ccccc1)C=CC(c1ccccc1)(c1ccccc1)O3] | | bromobenzene | 91 | 1,1-diphenyl-2-propyn-1-ol | 79 |

TABLE 1-continued

| Ex. # | Structure | Indole Core | Yield[1] (%) | N-Coupling component | Propargyl Alcohol | Yield[2] (%) |
|---|---|---|---|---|---|---|
| 3 | 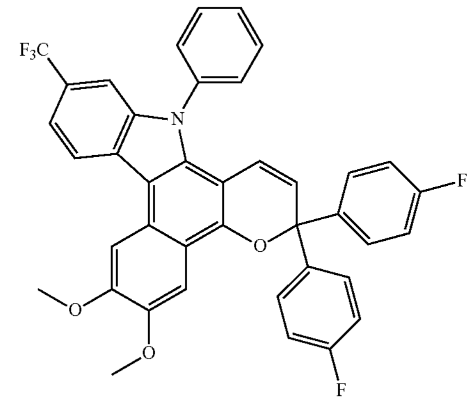 [SMILES: COc1cc2c3c(c4c(c2cc1OC)c1ccc(C(F)(F)F)cc1n4-c1ccccc1)C=CC(c1ccc(F)cc1)(c1ccc(F)cc1)O3] | | 91 | bromobenzene | 1,1-bis(4-fluorophenyl)-2-propyn-1-ol | 63 |
| 4[3] | 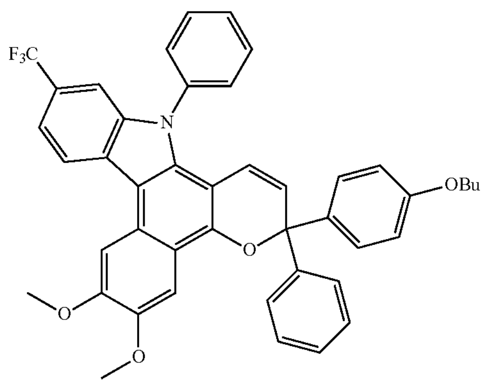 | | 91 | bromobenzene | 1-(4-butoxyphenyl)-1-phenyl-2-propyn-1-ol | 60 |

TABLE 1-continued

| Ex. # | Structure | Indole Core | N-Coupling component | Yield[1] (%) | Propargyl Alcohol | Yield[2] (%) |
|---|---|---|---|---|---|---|
| 5 | 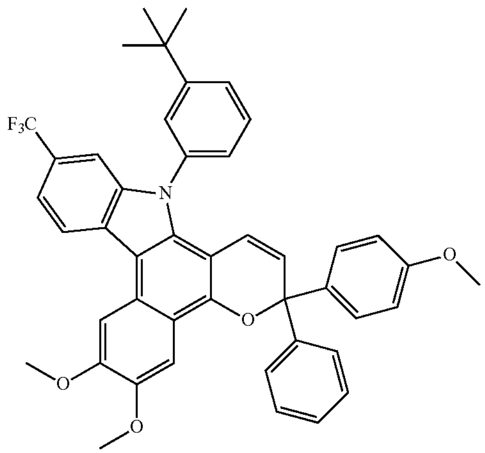 | | | 90 | | 52 |
| 6 | 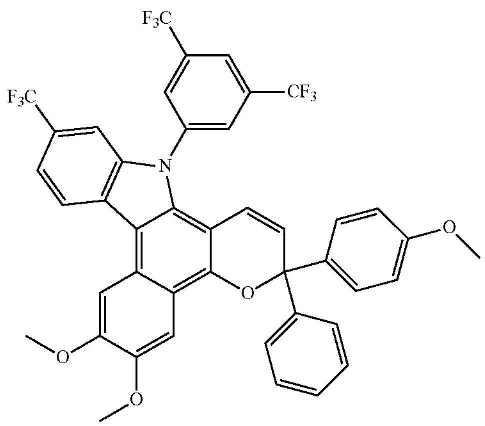 | | | 89 | | 84 |

TABLE 1-continued

| Ex. # | Structure | Indole Core | N-Coupling component | Yield[1] (%) | Propargyl Alcohol | Yield[2] (%) |
|---|---|---|---|---|---|---|
| 7 | 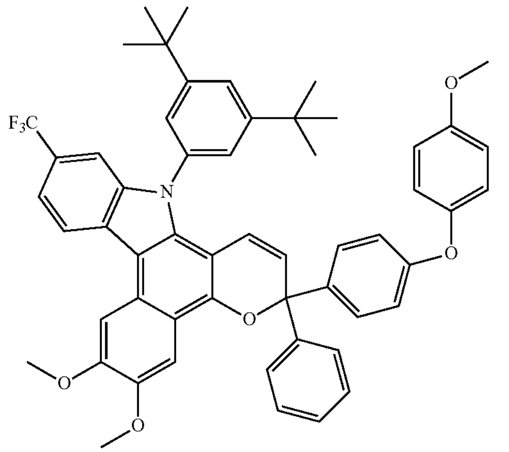 | | | 50 | | 74 |
| 8[3] | 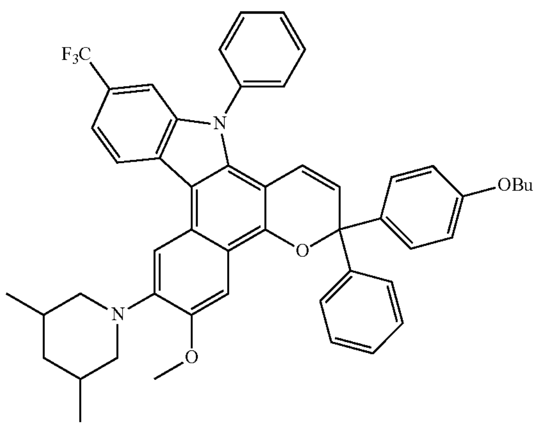 | N/A | N/A. | N/A. | N/A. | 20 |

TABLE 1-continued

| Ex. # | Structure | Indole Core | N-Coupling component | Yield¹ (%) | Propargyl Alcohol | Yield² (%) |
|---|---|---|---|---|---|---|
| 9 | 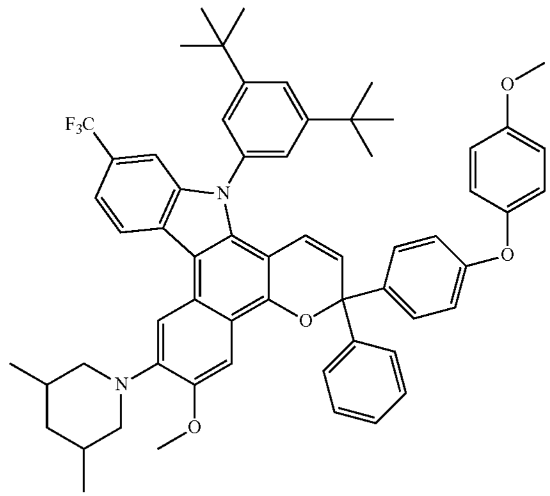 | N/A | N/A | N/A | N/A | 31 |
| 10 | 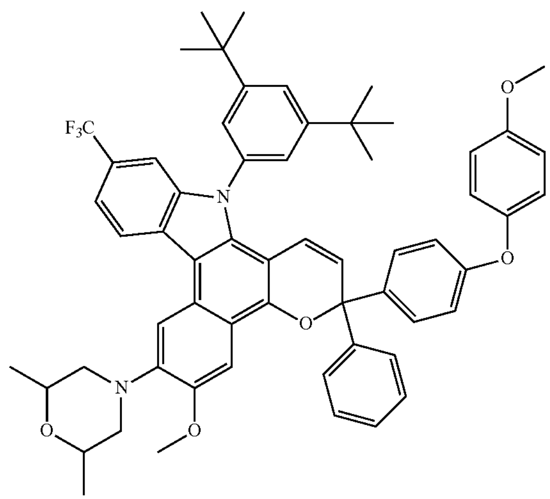 | N/A | N/A | N/A. | N/A. | 65 |

TABLE 1-continued

| Ex. # | Structure | Indole Core | N-Coupling component | Yield[1] (%) | Propargyl Alcohol | Yield[2] (%) |
|---|---|---|---|---|---|---|
| 11 | (structure) | (indole core) | n-butyl bromide | 88 | 1-(4-methoxyphenyl)-1-phenyl-prop-2-yn-1-ol | 18 |
| 12 | (structure) | (indole core) | bromobenzene | 99 | 1,1-bis(4-methoxyphenyl)-prop-2-yn-1-ol | 56 |

TABLE 1-continued

| Ex. # | Structure | Indole Core | N-Coupling component | Yield¹ (%) | Propargyl Alcohol | Yield² (%) |
|---|---|---|---|---|---|---|
| 13 | 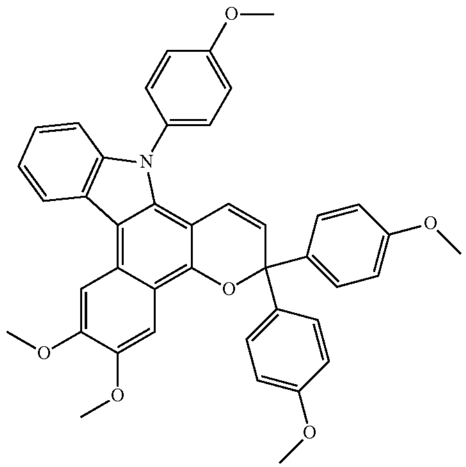 | | | 86 | | 34 |
| 14 | 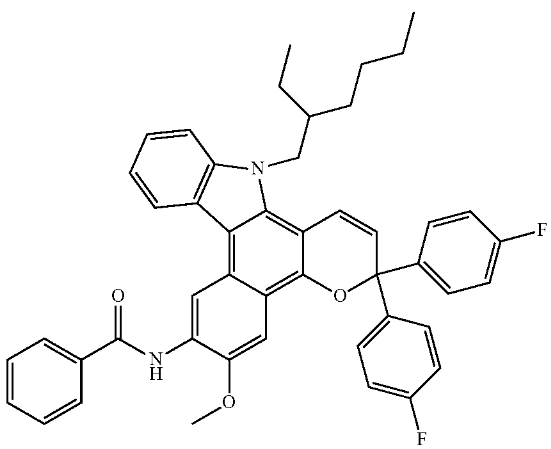 [SMILES: CCCCC(CC)Cn1c2ccccc2c2c3cc(NC(=O)c4ccccc4)c(OC)cc3c3c(c21)C=CC(c1ccc(F)cc1)(c1ccc(F)cc1)O3] | | | 84 | | 40 |

TABLE 1-continued
| Ex. # | Structure | Indole Core | N-Coupling component | Yield[1] (%) | Propargyl Alcohol | Yield[2] (%) |
|---|---|---|---|---|---|---|
| 15 | 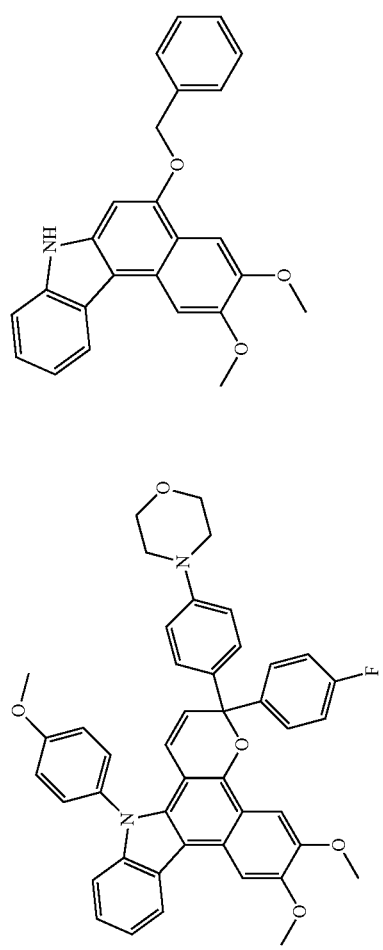 | 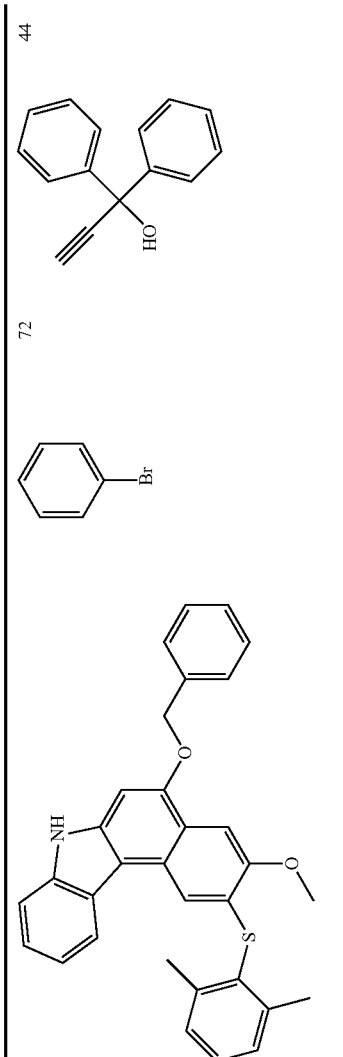 | 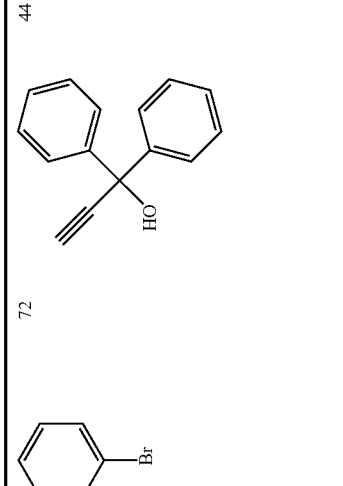 | 72 | 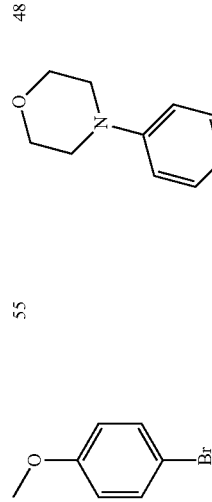 | 44 |
| CE1 | 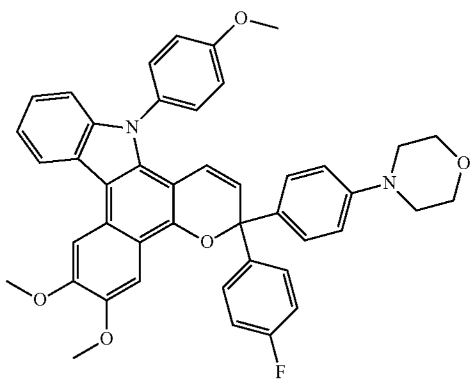 [SMILES: COc1ccc(-n2c3ccccc3c3c4cc(OC)c(OC)cc4c4c(c32)C=CC(c2ccc(F)cc2)(c2ccc(N3CCOCC3)cc2)O4)cc1] | 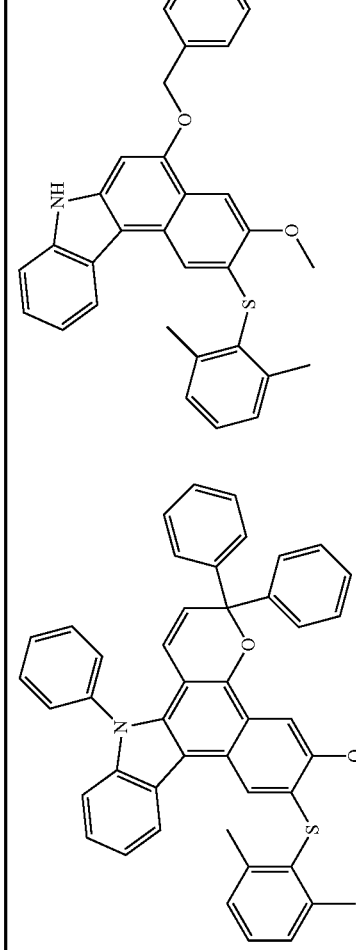 |  | 55 | 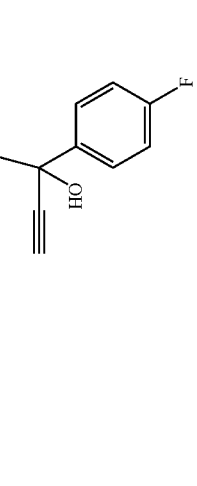 | 48 |

TABLE 1-continued

| Ex. # | Structure | Indole Core | N-Coupling component | Yield¹ (%) | Propargyl Alcohol | Yield² (%) |
|---|---|---|---|---|---|---|
| CE2 | 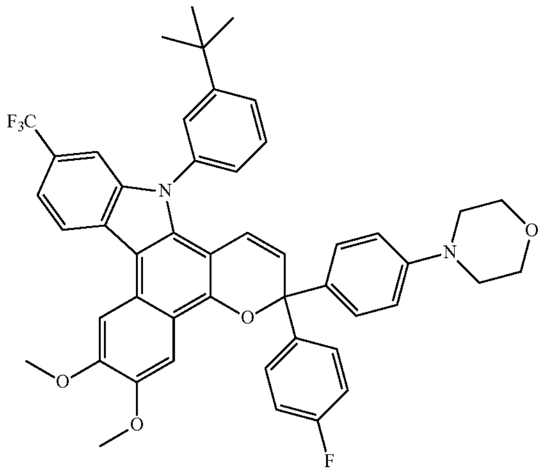 [SMILES: COc1cc2c3c(c4c(c2cc1OC)c1ccc(C(F)(F)F)cc1n4-c1cccc(C(C)(C)C)c1)C=CC(c1ccc(F)cc1)(c1ccc(N2CCOCC2)cc1)O3] | | | 90 | | 57 |
| CE3[5] | 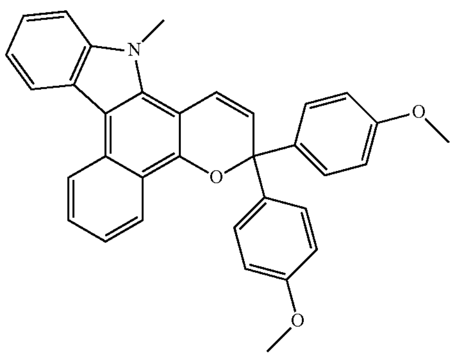 [SMILES: COc1ccc(C2(c3ccc(OC)cc3)C=Cc3c(c4ccccc4c4c5ccccc5n(C)c34)O2)cc1] | | | 85 | | 71 |

TABLE 1-continued

| Ex. # | Structure | Indole Core | N-Coupling component | Yield[1] (%) | Propargyl Alcohol | Yield[2] (%) |
|---|---|---|---|---|---|---|
| CE4 | 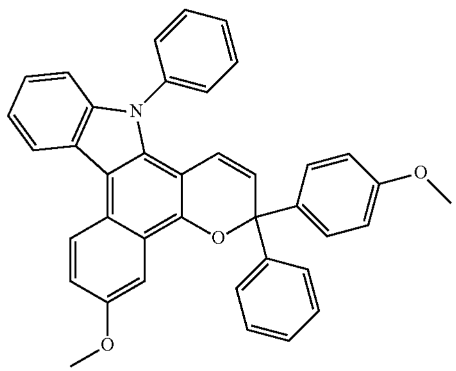 [SMILES: COc1ccc(C2(c3ccccc3)C=Cc3c(c4cc(OC)ccc4c4c5ccccc5n(-c5ccccc5)c34)O2)cc1] | | | 82 | | 76 |
| CE5 | 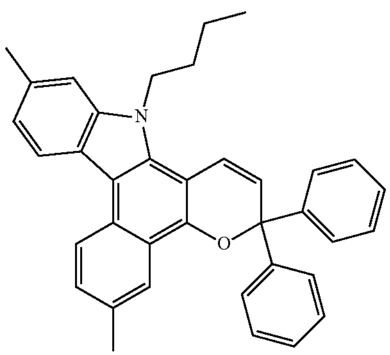 [SMILES: CCCCn1c2cc(C)ccc2c2c3ccc(C)cc3c3c(c21)C=CC(c1ccccc1)(c1ccccc1)O3] | | | 96 | | 46 |

[1]Yield corresponds to isolated intermediate prior to deprotection and propargyl alcohol addition (Formula IIIg).
[2]Yield corresponds to isolated dye compound (Formula Ia).
[3]Bu refers to n-butyl.
Entries marked "N/A" are not applicable to the Example.

TABLE 2

| Ex. # | Structure | Starting Indole-naphthopyran Component | Amination Component |
|---|---|---|---|
| 8 | 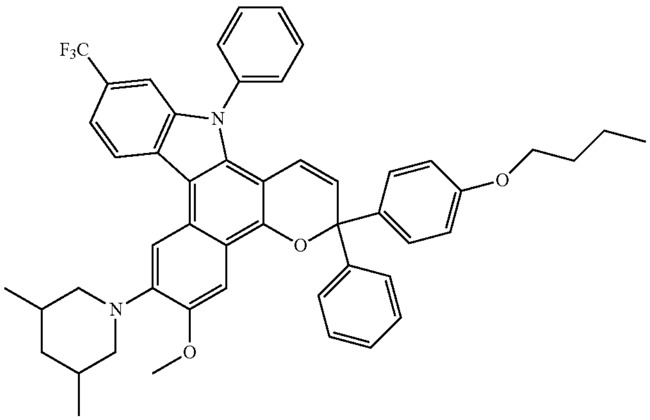 [SMILES: CCCCOc1ccc(C2(c3ccccc3)C=Cc3c(c4cc(OC)c(N5CC(C)CC(C)C5)cc4c4c5ccc(C(F)(F)F)cc5n(-c5ccccc5)c34)O2)cc1] | Example 4 | 3,5-dimethylpiperidine |
| 9 | 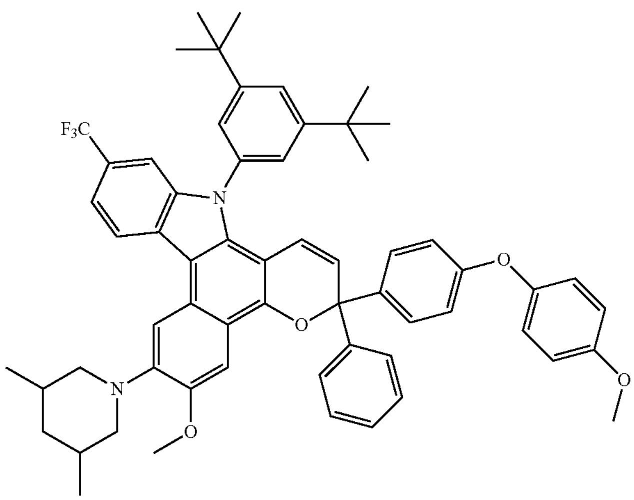 [SMILES: COc1ccc(Oc2ccc(C3(c4ccccc4)C=Cc4c(c5cc(OC)c(N6CC(C)OC(C)C6)cc5c5c6ccc(C(F)(F)F)cc6n(-c6cc(C(C)(C)C)cc(C(C)(C)C)c6)c45)O3)cc2)cc1] | Example 7 | 3,5-dimethylpiperidine |
| 10 | 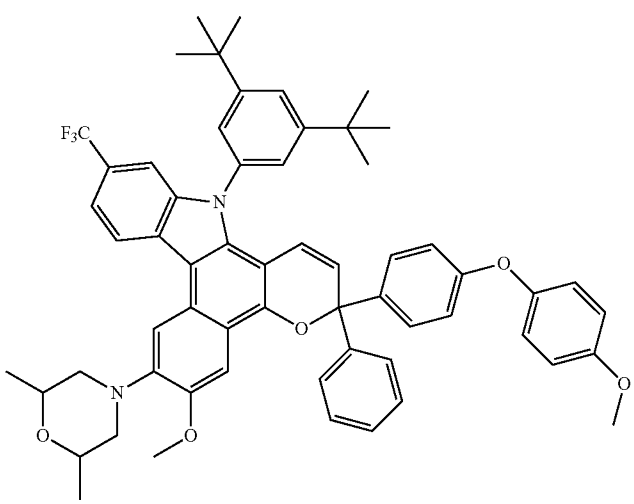 | Example 7 | 2,6-dimethylmorpholine |

Part 2: Results

Each of the photochromic dyes from Examples 1 through 14 and 24 through 31, and each comparative example shown in Table 4 were incorporated into a polyurethane coating systems as described in U.S. Pat. No. 8,608,988 examples 1-3 at the same mol % and applied at the same coating thickness on to 2"×2" test chips made from CR-39® monomer (PPG Industries, Inc.). All coated test chips were cured at 125° C. for 1 hour.

Each of the coated test chips was conditioned by first being exposed to 365-nanometer ultraviolet light for 10 minutes at a distance of about 14 centimeters to activate the photochromic materials within the coating. The UVA (315 to 380 nm) irradiance at the chip was measured with a LICOR® Model Li-1800 spectroradiometer and found to be 22.2 watts per square meter. Each of the test chips was then placed under a 500 watt, high intensity halogen lamp for 10 minutes at a distance of about 36 centimeters to bleach (inactivate) the photochromic materials. The illuminance at chip was measured with the LICOR® spectroradiometer and found to be 21.9 Klux. The coated test chips then were kept in a dark environment at room temperature (i.e., from 70 to 75° F., or 21 to 24° C.) for at least 1 hour prior to testing on an optical bench. Prior to optical bench measurement, the coated test chips were measured for ultraviolet absorbance at 390 nanometers.

Percent transmission (% T) for all the examples was determined using the CIE Y value in accordance with CIE 15: 2004 colorimetry using a D 65 illuminant and 10° observer. Where applicable, the a* and b* values as used herein in the specification and the claims refers to the a* and b* values measured in accordance with in accordance with CIE 15: 2004 space colorimetry, employing a D 65 illuminant and 10° observer, using the Hunter UltraScan Pro unit.

The BMP optical bench was fitted with two 150-watt ORIEL® Model #66057 Xenon arc lamps at right angles to each other. The light path from Lamp 1 was directed through a 3 mm SCFIOTT® KG-2 band-pass filter and appropriate neutral density filters that contributed to the required UV and partial visible light irradiance level. The light path from Lamp 2 was directed through a 3 mm SCFIOTT® KG-2 band-pass filter, a SCFIOTT® short band 400 nm cutoff filter and appropriate neutral density filters in order to provide supplemental visible light illuminance. A 2 inch×2 inch 50% polka dot beam splitter, at 45° to each lamp is used to mix the two beams. The combination of neutral density filters and voltage control of the Xenon arc lamp were used to adjust the intensity of the irradiance. Proprietary software i.e., BMPSoft version 2.1e, was used on the BMP to control timing, irradiance, air cell and sample temperature, shuttering, filter selection and response measurement. A ZEISS® spectrophotometer, Model MCS 501, with fiber optic cables for light delivery through the sample was used for response and color measurement. Photopic response measurements were collected on each coated test chip. The power output of the optical bench, i.e., the dosage of light that the test chip was exposed to, was adjusted to 6.7 Watts per square meter (W/m$^2$) UVA, integrated from 315-380 nm and 50 Klux illuminance, integrated from 380-780 nm. Measurement of this power setpoint was made using an irradiance probe and the calibrated Zeiss spectrophotometer. The sample cell was fitted with a quartz window and self-centering sample holder. The temperature in the sample cell was controlled at 23° C. through the software with a modified Facis, Model FX-10, environment simulator. Measurement of the sample's dynamic photochromic response and color measurements was made using the same Zeiss spectrophotometer, with fiber optic cables for light delivery from a tungsten halogen lamp and through the sample. The collimated monitoring light beam from the fiber optic cable was maintained perpendicular to the test sample while passing through the sample and directed into a receiving fiber optic cable assembly attached to the spectrophotometer. The exact point of placement of the sample in the sample cell was where the activating xenon arc beam and the monitoring light beam intersected to form two concentric circles of light. The angle of incidence of the xenon arc beam at the sample placement point was=30° from perpendicular.

Response measurements, in terms of a change in optical density ($\Delta$OD) from the unactivated or bleached state to the activated or colored state were determined by establishing the initial unactivated transmission, opening the shutter from the Xenon lamp(s) and measuring the transmission through activation at selected intervals of time. The change in optical density was determined according to the formula: $\Delta$OD=log(10)(% Tb/% Ta), where % Tb is the percent transmission in the bleached state, % Ta is the percent transmission in the activated state. The $\Delta$OD at saturation is after 15 minutes of activation and the Fade Half Life ("T½") value is the time interval in seconds for the $\Delta$OD of the activated form of the photochromic material in the coating to reach one half the fifteen minute $\Delta$OD at 73.4° F. (23° C.), after removal of the activating light source.

Fatigue Testing

Procedures for Fatigue Testing and results prior to initial performance testing were determined on an optical bench. The coated test chips were conditioned by exposing them to 365 nm ultraviolet light for 15 minutes at a distance of about 14 cm from the source in order to activate the photochromic molecules. The UVA irradiance at the test chip was measured with a Licor Model Li-1800 spectroradiometer and found to be 22.2 Watts per square meter. The test chip samples were then placed into an oven at 75° C. for 1 hour. The coated test chip samples then were exposed to room light for 3 hours. Finally, the coated test chips were then kept in a dark environment for at least 1 hour prior to testing in order to continue to fade back to a ground state prior to testing.

An optical bench fitted with a Schott 3 mm KG-2 band-pass filter, neutral density filter(s) and a Newport Model #67005 300-watt Xenon arc lamp with Model #69911 power supply in association with a Newport Model 689456 Digital Exposure/Timer was used to control the intensity of the irradiance beam utilized for activation of each coated test chip sample. A Uniblitz model #CS25S3ZMO high-speed shutter with model #VMM-D3 controller, and fused silica condensing lenses for activation beam collimation and focusing through a quartz water cell/sample holder for maintaining sample temperature in which each test chip to be tested was inserted. The temperature in the water cell was controlled with a pumped water circulation system in which the water passed through copper coils that were placed in the reservoir of a chiller unit. The water cell used to hold test chip samples contained fused silica sheets on the front and back facings in order to eliminate spectral change of the activation or monitoring light beams. The filtered water passing through the water cell was maintained at 100° F.±2° for photochromic testing before and after exposure to the Atlas Weatherometer.

A custom made broadband light source for monitoring response measurements was positioned in a perpendicular manner to a surface of the cell assembly. This broad beam light source is obtained by collecting and combining separately filtered light from a 100-Watt tungsten halogen lamp (controlled by a Lambda UP60-14 constant voltage power supply) with a split-end, bifurcated fiber optical cable to enhance the short wavelength light intensity. After passing through the test sample, this monitoring light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

An International Light Research Radiometer, Model IL-1700 with a detector system comprising a Model SED033 detector, B Filter and diffuser was used to verify the irradiance prior to testing. An adjusted value of 18.0 W/m$^2$ was used as the irradiance verification set point. The output display of the radiometer was corrected (factor values set) against a Licor 1800-02 Optical Calibration Calibrator in order to display values representing Watts per square meter UVA. Increasing or decreasing the current to the lamp through the controller and/or by adding or removing neutral density filters in the activation light path was done to make adjustments to the xenon lamp output. The test chip samples were exposed to activation light at 31° normal to the surface of the test sample.

The change in optical density (ΔOD) from the bleached first state to the darkened second state was determined by establishing the initial transmission, opening the shutter from the Xenon lamp to provide ultraviolet radiation to change the test chip sample from the bleached first state to an activated second (i.e., colored) state and measuring the transmission in the activated state after typically 5 minutes of activation. The change in optical density is calculated using the formula: ΔOD log(% Tb/% Ta), where % Tb is the percent transmission in the bleached first state, % Ta is the percent transmission in the activated state and the logarithm is to the base 10. This provided the $OD_{init}$.

An Atlas Ci4000 weatherometer was used for conducting the simulated solar radiation accelerated weathering. The test chip samples were exposed for a 1 hour dark cycle and then a 65 hour light cycle using a boro/boro silicate filtered Xenon arc lamp with an output of 0.25 Watts per square meter at 340 nm. The temperature in the weatherometer was maintained at 45° C. and the relative humidity was controlled at 70% humidity. The temperature of the black panel was maintained at 55° C.

After the test chip samples underwent this UV exposure fatigue cycle, the samples were preconditioned as described above and measured on the optical bench to obtain the final $\Delta OD_{final}$ under the same conditions as described for the initial testing.

The percent fatigue was determined by measuring the difference between the change in optical density (ΔOD) of the test chip sample before and after accelerated weathering according to the formula:

% Fatigue=$(\Delta OD_{init} - \Delta OD_{final}/\Delta OD_{init}) \times 100$.

The ΔOD at saturation is after 15 minutes of activation and the Fade Half Life ("T½") value is the time interval in seconds for the ΔOD of the activated form of the photochromic-dichroic material in the coating to reach one half the fifteen-minute ΔOD at 73.4° F. (23° C.), after removal of the activating light source.

Two absorption maxima ΔOD are observed for the indolenaphthopyran compounds of the present invention at full activation. Wavelength A ("λ A") is the wavelength with the maximum ΔOD between 420-500 nm and Wavelength B ("λ B") is the wavelength with maximum ΔOD between 500-650 nm. The A band to B band absorption ratio ("A-B ratio") is calculated by the formula:

A-B Ratio=max ΔOD wavelength A/max ΔOD wavelength A.

Table 3 shows the absorption data for Examples 1 to 15 and comparative examples CE1 to CE7. Structures for Examples 1 to 15 and CE1 to CE5 can be found in Table 1.

TABLE 3

| Ex. # | Structure | λ A (nm) | max ΔOD λ A | λ B (nm) | max ΔOD λ B | A-B Ratio |
|---|---|---|---|---|---|---|
| 1 | | 430 | 1.14 | 571 | 0.18 | 6.33 |
| 2 | | 438 | 0.92 | 567 | 0.18 | 5.11 |
| 3 | | 438 | 0.89 | 570 | 0.16 | 5.56 |
| 4 | | 455 | 0.69 | 566 | 0.18 | 3.83 |
| 5 | | 457 | 1.15 | 568 | 0.29 | 3.97 |
| 6 | | 457 | 0.88 | 561 | 0.25 | 3.52 |
| 7 | | 455 | 0.90 | 654 | 0.23 | 3.91 |
| 8 | | 473 | 1.14 | 570 | 0.19 | 6.0 |
| 9 | | 471 | 1.95 | 570 | 0.31 | 6.3 |
| 10 | | 468 | 1.81 | 570 | 0.31 | 5.8 |
| 11 | | 449 | 1.28 | 586 | 0.25 | 5.12 |
| 12 | | 467 | 0.76 | 581 | 0.22 | 3.45 |
| 13 | | 469 | 0.93 | 584 | 0.26 | 3.58 |
| 14 | | 446 | 1.18 | 591 | 0.23 | 5.05 |
| 15 | | 450 | 1.26 | 582 | 0.26 | 4.85 |
| CE1 | | 488 | 0.82 | 570 | 0.35 | 2.34 |
| CE2 | | 494 | 0.8 | 570 | 0.4 | 2.00 |
| CE3 | | 453 | 0.54 | 565 | 0.27 | 2.00 |
| CE4 | | 457 | 0.85 | 585 | 0.37 | 2.30 |
| CE5 | | 437 | 1.07 | 575 | 0.459 | 2.33 |

TABLE 3-continued

| Ex. # | Structure | λ A (nm) | max ΔOD λ A | λ B (nm) | max ΔOD λ B | A-B Ratio |
|---|---|---|---|---|---|---|
| CE6 | 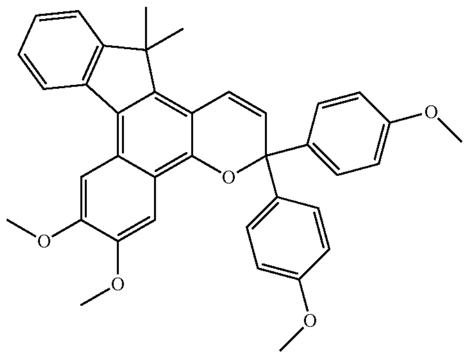 | 452 | 1.47 | 568 | 0.89 | 1.65 |
| CE7 | 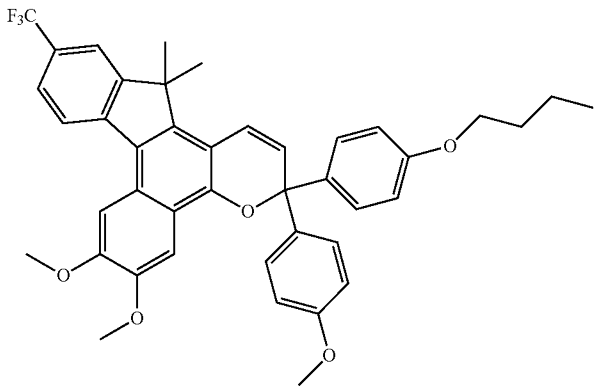 [SMILES: CCCCOc1ccc(C2(c3ccc(OC)cc3)C=Cc3c4c(c5cc(OC)c(OC)cc5c3O2)-c2ccc(C(F)(F)F)cc2C4(C)C)cc1] | 455 | 0.94 | 567 | 0.57 | 1.65 |

The results shown in Table 3 clearly demonstrate the improvement in A-B Ratio, indicating enhanced blue light blocking properties, provided by compounds of the present invention compared to similar compounds outside the scope of the invention. For example, the indolenaphthopyran compounds of the present invention have higher A-B Ratios than compounds which do not have B and B' groups having a Hammett $\sigma_p$ value of greater than −0.50, such as CE1 and CE2. Indolenaphthopyran compounds of the present invention also exhibit higher A-B Ratios than compounds lacking both $R^1$ and $R^2$ substituents at the 6- and 7-positions, such as CE3 to CE5. The indolenaphthopyran compounds of the present invention also have higher A-B Ratios than similarly substituted indenonaphthopyran compounds, such as CE 6 and CE7.

Table 4 shows the results of the fatigue testing for Examples 1-15 and Comparative Examples CE8 and CE9. Structures for Examples 1-15 can be found in Table 1.

TABLE 4

| | | Activated state | | | | |
|---|---|---|---|---|---|---|
| Ex. # | Structure | % T | a* | b* | Fade T½ (sec) | % Fatigue |
| 1 | | 60.0 | −14.7 | 56.4 | 68 | 10.8 |
| 2 | | 60.5 | −11.3 | 53.6 | 39 | 10 |
| 3 | | 61.7 | −12.0 | 53.8 | 36 | 10.7 |
| 4 | | 56.0 | −2.4 | 45.6 | 20 | 4.1 |
| 5 | | 42.3 | 0.1 | 58.6 | 41 | 2.4 |
| 6 | | 47.8 | 0.4 | 48.2 | 31 | 6.0 |
| 7 | | 48.8 | −0.5 | 52.5 | 75 | 7.2 |
| 8 | | 42.7 | 19.9 | 62.7 | 27 | 3.5 |
| 9 | | 31.2 | 26.3 | 79.5 | 107 | 5.3 |
| 10 | | 33.7 | 18.8 | 77.1 | 90 | 5.3 |
| 11 | | 45.3 | −9.1 | 71.6 | 67 | 4.0 |
| 12 | | 43.4 | 2.9 | 41.5 | 22 | 2.8 |
| 13 | | 37.9 | 5.2 | 46.0 | 34 | 6.5 |
| 14 | | 52.3 | −14.0 | 70.4 | 66 | — |
| 15 | | 47.5 | −11.0 | 69.8 | 68 | 9.6 |

TABLE 4-continued

| Ex. # | Structure | Activated state % T | a* | b* | Fade T½ (sec) | % Fatigue |
|---|---|---|---|---|---|---|
| CE8 | 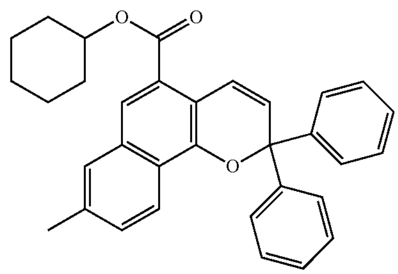 [SMILES: Cc1ccc2c3c(c(C(=O)OC4CCCCC4)cc2c1)C=CC(c1ccccc1)(c1ccccc1)O3] | 71.6 | 10.3 | 35.1 | 30 | 92.8 |
| CE9 | 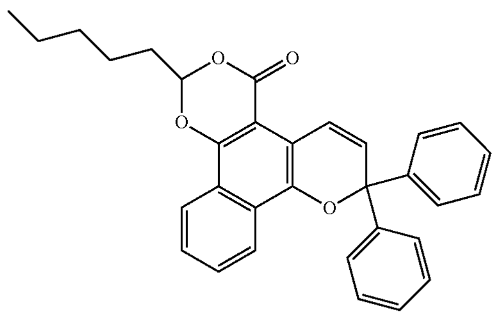 [SMILES: CCCCCC1OC(=O)c2c3c(c4ccccc4c2O1)OC(c1ccccc1)(c1ccccc1)C=C3] | 60.3 | 21.3 | 85.2 | 184 | 83.5 |

The results shown in Table 4 demonstrate that the compounds of the present invention provide excellent fade rates as well as fatigue resistance, indicated by low values for % Fatigue. These results also demonstrate that the compounds of the present invention provide improved fatigue resistance compared to photochromic compounds having similar yellow color in the activated state, such as CE8 and CE9.

The present invention can be further characterized by one or more of the following non-limiting clauses.

Clause 1. An indolenaphthopyran, having the core skeletal structure represented by Formula (Ia):

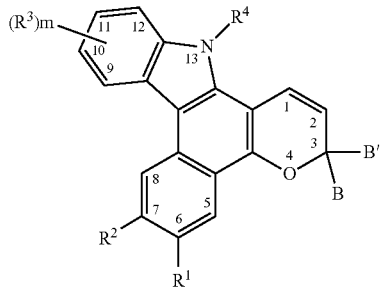

Formula (Ia)

wherein, $R^1$ and $R^2$ are each independently substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, a nitrogen containing heterocycle, substituted or unsubstituted alkyl, substituted or unsubstituted aryl, —NHC(O)$R^a$, or —OC(O)$R^a$, wherein $R^a$ is substituted or unsubstituted alkyl, substituted or unsubstituted aryl, substituted or unsubstituted heteroaryl, substituted or unsubstituted alkoxy, substituted or unsubstituted aryloxy, substituted or unsubstituted alkylthio, or substituted or unsubstituted arylthio;

$R^4$ is selected from hydrogen, substituted or unsubstituted alkyl, substituted or unsubstituted heterocycloalkyl, allyl, substituted or unsubstituted aryl, or substituted or unsubstituted heteroaryl;

B and B' are each independently substituted or unsubstituted aryl, or substituted or unsubstituted heteroaryl, wherein each substituted aryl or substituted heteroaryl is substituted with a group having a Hammett $\sigma_p$ value of greater than −0.50;

m is 0 to 4; and $R^3$ is hydrogen or a group other than hydrogen.

Clause 2. The indolenaphthopyran of clause 1, wherein, $R^1$ is substituted or unsubstituted alkoxy, and $R^2$ is substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, or a nitrogen-containing heterocycle.

Clause 3. The indolenaphthopyran of clauses 1 or 2, wherein B and B' are each independently substituted aryl or substituted heteroaryl with a group having a Hammett $\sigma_p$ value of −0.5 to 0.8.

Clause 4. The indolenaphthopyran of any of clauses 1 to 3, wherein B and B' are each independently substituted or unsubstituted phenyl.

Clause 5. The indolenaphthopyran of clause 4, wherein each phenyl substituent is in each case independently alkoxy, halo, alkyl, or aryloxy.

Clause 6. The indolenaphthopyran of any of clauses 1 to 5, wherein $R^1$ and $R^2$ taken together form a cyclic structure.

Clause 7. The indolenaphthopyran of any of clauses 1 to 6, wherein $R^4$ is substituted or unsubstituted phenyl or substituted or unsubstituted alkyl.

Clause 8. The indolenaphthopyran of any of clauses 1 to 7, wherein,
m is 0 to 4; and
$R^3$ independently for each m is
i. hydroxyl;
ii. cyano;
iii. (meth)acrylate;
iv. amino or nitrogen-containing heterocycle;
v. a mesogen-containing group $L^1$;
vi. substituted or unsubstituted alkyl;
vii. substituted or unsubstituted alkenyl;
viii. substituted or unsubstituted alkynyl;
ix. a halo group;
x. a perhalo group;
xi. boronic ester or boronic acid;
xii. polyether, polyester, polycarbonate, or polyurethane;
xiii. substituted or unsubstituted aryl;
xiv. substituted or unsubstituted heterocycloalkyl;
xv. substituted or unsubstituted heteroaryl;
xvi. substituted or unsubstituted alkoxy or substituted or unsubstituted aryloxy;
xvii. substituted or unsubstituted alkylthio or substituted or unsubstituted arylthio;
xviii. ketone, aldehyde, ester, carboxylic acid, carboxylate, or amide;
xix. carbonate, carbamate, or urea; or
xx. siloxane, alkoxysilane, or polysiloxane.

Clause 9. The indolenaphthopyran of clause 8, wherein $R^3$ is at the 11-position.

Clause 10. The indolenaphthopyran of clauses 8 or 9, wherein $R^3$ is at the 10-position and is a mesogen-containing group $L^1$.

Clause 11. The indolenaphthopyran of any of clauses 8 to 10, wherein $R^3$ is cyano; a halo group; haloalkyl; perhaloalkyl; substituted or unsubstituted aryl; or substituted or unsubstituted heteroaryl.

Clause 12. The indolenaphthopyran of any of clauses 8 to 11, wherein each mesogen-containing group $L^1$ is independently represented by the following Formula (II),

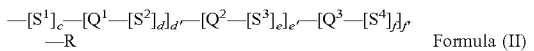

$$-[S^1]_c-[Q^1-[S^2]_d]_{d'}-[Q^2-[S^3]_e]_{e'}-[Q^3-[S^4]_f]_{f'}-R \quad \text{Formula (II)}$$

wherein,
(a) $Q^1$, $Q^2$, and $Q^3$ for each occurrence, are independently a divalent group selected from the group consisting of unsubstituted aryl, substituted aryl, unsubstituted cycloalkyl, and substituted cycloalkyl;
wherein the aryl substituents and cycloalkyl substituents are each independently selected from the group consisting of liquid crystal mesogens, halogen, alkyl, alkoxy, alkylamino, dialkylamino, alkylthio, alkoxycarbonyl, alkylcarbonyl, alkoxycarbonyloxy, aryloxycarbonyloxy, perfluoroalkyl, and perfluoroalkoxy;
(b) c, d, e, and f are each independently an integer of 0 to 3; and each $S^1$, $S^2$, $S^3$, and $S^4$ is independently chosen for each occurrence from a spacer unit selected from the group consisting of:
(i) —C(Z)$_2$—, —N(Z)—, —C(Z)=C(Z)—, —C(Z)=N—, wherein Z for each occurrence is independently selected from the group consisting of hydrogen, alkyl, or aryl;
(ii) —Si(CH$_3$)$_2$—, —Si(CH$_3$)$_2$O—; and
(iii) —O—, —C(=O)—, —C≡C—, —N=N—, —S—, —S(=O)—, —(O=)S(=O)—, —(O=)S(=O)O—, —O(O=)S(=O)O— provided that when two spacer units comprising heteroatoms are linked together the spacer units are linked so that heteroatoms are not directly linked to each other;
(c) R is alkyl; and
(d) d', e' and f' are each independently 0, 1, 2, 3, and 4, provided that the sum of d'+e'+f' is at least 1.

Clause 13. The indolenaphthopyran of any of clauses 1 to 12 wherein the formula comprises at least one additional substituent, identical or different, located on at least one available position on the core skeletal structure among positions 1, 2, 3, 5, 6, 7, 8, 9, 10, 11, 12, or 13 depicted therein.

Clause 14. The indolenaphthopyran of clause 13, wherein said at least one additional substituent is independently selected from alkyl group, heterocycloalkyl group, aryl group, heteroaryl group, thiol groups, alkylthio groups, arylthio groups, ketone groups, aldehyde groups, ester groups, carboxylic acid groups, phosphoric acid groups, phosphoric acid ester groups, sulfonic acid groups, sulfonic acid ester groups, nitro groups, cyano groups, alkyl groups, aralkyl groups, alkenyl groups, alkynyl groups, haloalkyl groups, perhaloalkyl groups, heterocycloalkyl groups, aryl groups, alkaryl groups, hydroxyl substituted aryl groups, alkoxy substituted aryl groups, heterocycloalkyl substituted aryl groups, halo substituted aryl groups, poly-fused-ring aryl groups, heteroaryl groups, poly-fused-ring heteroaryl groups, amine groups, carboxylate groups, siloxane groups, alkoxysilane groups, polysiloxane groups, amide groups, carbamate groups, carbonate groups, urea groups, polyester groups, polyether groups, polycarbonate groups, polyurethane groups, acrylate groups, methacrylate groups, aryl amino groups, cyclic amino groups, heteroaromatic groups, or combinations thereof.

Clause 15. The indolenaphthopyran of any of clauses 1 to 14, having a bimodal absorption profile wherein the A band to B band absorption ratio ranges from 3.0 to 7.0:1.

Clause 16. A photochromic composition comprising the indolenaphthopyran of any of clauses 1 to 15.

Clause 17. A photochromic article comprising the indolenaphthopyran of any of clauses 1 to 15, wherein the photochromic article is selected from the group consisting of ophthalmic articles, display articles, windows, mirrors, active liquid crystal cell articles, and passive liquid crystal cell articles; or
wherein the photochromic article is an ophthalmic article selected from the group consisting of corrective lenses, non-corrective lenses, contact lenses, intra-ocular lenses, magnifying lenses, protective lenses, and visors; or
wherein the photochromic article is a display article selected from the group consisting of screens, monitors, and security elements.

Clause 18. The use of an indolenaphthopyran of any of clauses 1 to 15 to prepare a photochromic article.

The present invention has been described with reference to specific details of particular embodiments thereof. It is not intended that such details be regarded as limitations upon the scope of the invention except insofar as to the extent that they are included in the accompanying claims.

What is claimed is:

1. A photochromic indolenaphthopyran comprising the core skeletal structure represented by Formula (I):

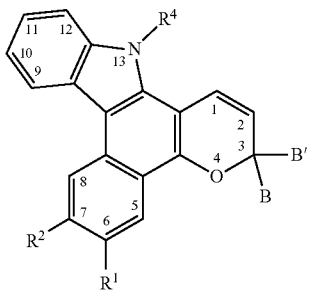

Formula (I)

wherein,
- $R^1$ and $R^2$ are each independently substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, a nitrogen containing heterocycle, substituted or unsubstituted alkyl, substituted or unsubstituted aryl, —NHC(O)$R^a$, or —OC(O)$R^a$,
  wherein $R^a$ is substituted or unsubstituted alkyl, substituted or unsubstituted aryl, substituted or unsubstituted heteroaryl, substituted or unsubstituted alkoxy, substituted or unsubstituted aryloxy, substituted or unsubstituted alkylthio, or substituted or unsubstituted arylthio;
- $R^4$ is selected from the group consisting of hydrogen, substituted or unsubstituted alkyl, substituted or unsubstituted heterocycloalkyl, allyl, substituted or unsubstituted aryl, and substituted or unsubstituted heteroaryl; and
- B and B' are each independently substituted or unsubstituted aryl, or substituted or unsubstituted heteroaryl, wherein each substituted aryl or substituted heteroaryl is substituted with a group having a Hammett $\sigma_p$ value of greater than −0.50.

2. The indolenaphthopyran according to claim 1, wherein, $R^1$ is substituted or unsubstituted alkoxy, and
$R^2$ is substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, or a nitrogen-containing heterocycle.

3. The indolenaphthopyran according to claim 1, wherein B and B' are each independently substituted aryl or substituted heteroaryl with a group having a Hammett $\sigma_p$ value of −0.5 to 0.8.

4. The indolenaphthopyran according to claim 1, wherein B and B' are each independently substituted or unsubstituted phenyl.

5. The indolenaphthopyran according to claim 4, wherein each phenyl substituent is in each case independently alkoxy, halo, alkyl, or aryloxy.

6. The indolenaphthopyran according to claim 1, wherein $R^1$ and $R^2$ form a cyclic structure.

7. The indolenaphthopyran according to claim 1, wherein $R^4$ is substituted or unsubstituted phenyl or substituted or unsubstituted alkyl.

8. The indolenaphthopyran of according to claim 1, having the core skeletal structure represented by Formula (Ia):

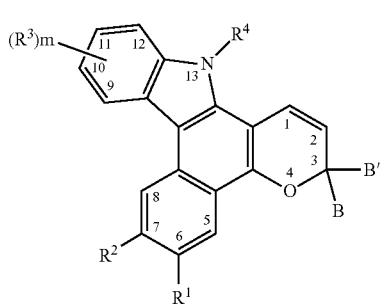

Formula (Ia)

wherein,
- m is 0 to 4; and
- $R^3$ independently for each m is
  i. hydroxyl;
  ii. cyano;
  iii. (meth)acrylate;
  iv. amino or nitrogen-containing heterocycle;
  v. a mesogen-containing group $L^1$;
  vi. substituted or unsubstituted alkyl;
  vii. substituted or unsubstituted alkenyl;
  viii. substituted or unsubstituted alkynyl;
  ix. a halo group;
  x. a perhalo group;
  xi. boronic ester or boronic acid;
  xii. polyether, polyester, polycarbonate, or polyurethane;
  xiii. substituted or unsubstituted aryl;
  xiv. substituted or unsubstituted heterocycloalkyl;
  xv. substituted or unsubstituted heteroaryl;
  xvi. substituted or unsubstituted alkoxy or substituted or unsubstituted aryloxy;
  xvii. substituted or unsubstituted alkylthio or substituted or unsubstituted arylthio;
  xviii. ketone, aldehyde, ester, carboxylic acid, carboxylate, or amide;
  xix. carbonate, carbamate, or urea; or
  xx. siloxane, alkoxysilane, or polysiloxane.

9. The indolenaphthopyran according to claim 8, wherein $R^3$ is at the 11-position.

10. The indolenaphthopyran according to claim 8, wherein $R^3$ is at the 10-position and is a mesogen-containing group L1.

11. The indolenaphthopyran of according to claim 8, wherein $R^3$ is cyano; a halo group; haloalkyl; perhaloalkyl; substituted or unsubstituted aryl; or substituted or unsubstituted heteroaryl.

12. The indolenaphthopyran of according to claim 8, wherein each the mesogen-containing group $L^1$, at one or more of positions 9, 10, 11, or 12, is independently represented by the following Formula (II),

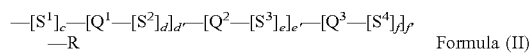

Formula (II)

wherein,
(a) $Q^1$, $Q^2$, and $Q^3$ for each occurrence, are independently a divalent group selected from the group consisting of unsubstituted aryl, substituted aryl, unsubstituted cycloalkyl, and substituted cycloalkyl;
wherein the aryl substituents and cycloalkyl substituents are each independently selected from the group consisting of liquid crystal mesogens, halogen, alkyl, alkoxy, alkylamino, dialkylamino, alkylthio, alkoxycarbonyl, alkylcarbonyl, alkoxycarbonyloxy, aryloxycarbonyloxy, perfluoroalkyl, and perfluoroalkoxy;

(b) c, d, e, and f are each independently an integer of 0 to 3; and each $S^1$, $S^2$, $S^3$ and $S^4$ is independently chosen for each occurrence from a spacer unit selected from the group consisting of:

(i) —C(Z)$_2$—, —N(Z)—, —C(Z)=C(Z)—, —C(Z)=N—, wherein Z for each occurrence is independently selected from the group consisting of hydrogen, alkyl, and aryl;

(ii) Si(CH$_3$)$_2$—, —Si(CH$_3$)$_2$O—; and (iii) —O—, —C(=O)—, —C≡C—, —N=N—, —S—, —S(=O)—, —(O=)S(=O)—, —(O=)S(=O)O—, —O(O=)S(=O)O— provided that when two spacer units comprising heteroatoms are linked together the spacer units are linked so that heteroatoms are not directly linked to each other;

(c) R is alkyl; and (d) d', e' and f' are each independently 0, 1, 2, 3, and 4, provided that the sum of d'+e'+f' is at least 1.

13. The indolenaphthopyran of according to claim 1, having a bimodal absorption profile having an A band to B band absorption ratio ranging from 3.0 to 7.0:1.

14. A photochromic composition comprising the indolenaphthopyran according to claim 1.

15. A photochromic article comprising the indolenaphthopyran according to claim 1, wherein the photochromic article is selected from the group consisting of ophthalmic articles, display articles, windows, mirrors, active liquid crystal cell articles, and passive liquid crystal cell articles; or wherein the photochromic article is an ophthalmic article selected from the group consisting of corrective lenses, non-corrective lenses, contact lenses, intra-ocular lenses, magnifying lenses, protective lenses, and visors; or wherein the photochromic article is a display article selected from the group consisting of screens, monitors, and security elements.

* * * * *

UNITED STATES PATENT AND TRADEMARK OFFICE
CERTIFICATE OF CORRECTION

PATENT NO. : 11,897,894 B2
APPLICATION NO. : 17/416006
DATED : February 13, 2024
INVENTOR(S) : Ryan Stayshich et al.

It is certified that error appears in the above-identified patent and that said Letters Patent is hereby corrected as shown below:

On the Title Page

Item (57), Column 1, Abstract, Line 1, delete "indolenapthtopyran" and insert
-- indolenaphthopyran --

In the Specification

Column 1, Line 2, below "INDOLENAPHTHOPYRANS" insert
-- CROSS-REFERENCE TO RELATED APPLICATION
This application is the United States national phase of International Application No. PCT/EP2018/086583 filed December 21, 2018, the disclosure of which is hereby incorporated by reference in its entirety. --

In the Claims

Column 66, Line 1, Claim 8, after "indolenaphthopyran" delete "of"

Column 66, Line 49, Claim 11, after "indolenaphthopyran" delete "of"

Column 66, Line 53, Claim 12, after "indolenaphthopyran" delete "of"

Column 68, Line 1, Claim 13, after "indolenaphthopyran" delete "of"

Signed and Sealed this
Twenty-fifth Day of June, 2024

Katherine Kelly Vidal
*Director of the United States Patent and Trademark Office*